(12) United States Patent
Miserez

(10) Patent No.: US 7,220,846 B1
(45) Date of Patent: May 22, 2007

(54) DNA POLYMORPHISMS IN STEROL REGULATOR ELEMENT BINDING PROTEINS

(76) Inventor: Andre R. Miserez, St. Jakobstrasse 70, Ch-4147 Aesch (CH)

( * ) Notice: Subject to any disclaimer, the term of this patent is extended or adjusted under 35 U.S.C. 154(b) by 737 days.

(21) Appl. No.: 10/030,504

(22) PCT Filed: Jul. 7, 2000

(86) PCT No.: PCT/IB00/00918

§ 371 (c)(1),
(2), (4) Date: Mar. 4, 2002

(87) PCT Pub. No.: WO01/04352

PCT Pub. Date: Jan. 18, 2001

(30) Foreign Application Priority Data

Jul. 9, 1999 (CH) ..................................... 1277/99

(51) Int. Cl.
*C07H 21/02* (2006.01)
*C12Q 1/68* (2006.01)

(52) U.S. Cl. .................. 536/23.1; 435/6; 536/22.1; 536/24.3; 536/24.31; 536/24.33

(58) Field of Classification Search ................ None
See application file for complete search history.

(56) References Cited

U.S. PATENT DOCUMENTS 5,891,631 A    4/1999    Goldstein et al. .............. 435/6

OTHER PUBLICATIONS

Wacholder et al (J. Natl. Cancer Institute (2004) 96(6):434-442).*
Lucentini et al (The Scientist (2004) vol. 18).*
Ioannidis (Nature genetics (2001) 29:306-309).*
Genbank Accession No. AC122129.*
Roy et al (Cell (1995) 80:167-178).*
http://bacpac.chori.org/clones.htm (accessed Dec. 2005).*
Yokoyama et al (Cell (1993) 75:187-197).*
Miserez et al. "Structure of the Human Gene Encoding Sterol Regulatory Element Binding Protein2 (SREBF2)" Genomics vol. 40, No. 1, 1997, 31-40, XP-002159138.
Miserez "Die Bedeutung genetisher Faktoren bei der Enstehung des Herzinfarkts", Uni Nova, Wissenschaftmagazin der Universität Basel, Online! vol. 81, Apr. 1998 (in German) XP-002159139.
Hua et al. "Stucture of the Human Gene Encoding . . . (SREBF1) and Localization . . . to Chromosomes 17p11.2 and 22q13" Genomics vol. 25, No. 3, 1995, pp. 667-673, XP-000979463.
Wang et al. "Cleavage of sterol regulatory element binding proteins (SREBPs) by CPP32 during apoptosis", The EMBO Journal, vol. 15, No. 5, 1996, pp. 1012-1020, XP-002159140.
Brown et al. "The SREBP Pathway: Regulation . . . by Proteolysis of a Membrane-Bound Transcription Factor", Cell, vol. 89, May 2, 1997, pp. 331-340, XP-002123067.
Shimano et al. "Elevated Levels of SREBP-2 . . . for a Targeted Disruption of the SREBP-1 Gene", Journal of Clinical Investigation, vol. 100, No. 8, 1997, pp. 2115-2124 XP-002931070.
Hacia et al. "Strategies for Mutational Analysis . . . Using High-Density Oligonucleotide Arrays", Genome Research, vol. 8, No. 12, Dec. 1998, pp. 1245-1258, XP-002925459.
Yang et al. "Three Different Rearrangements . . . and Produce Sterol-resistant Phenotype in Three Cell Lines", JBC Online, vol. 270, No. 20, May 19, 1995, pp. 12152-12161.
Pai et al. "Differential Stimulation of Cholesterol . . . Expressing Individual Nuclear Sterol Regulatory Element-binding Proteins", Journal of Bio. Chem., vol. 273, No. 40, Oct. 2, 1998, pp. 26138-26148.

* cited by examiner

*Primary Examiner*—Jeffrey Fredman
(74) *Attorney, Agent, or Firm*—Cooper & Dunham LLP

(57) ABSTRACT

The invention relates to DNA polymorphisms in sterol regulator element binding proteins (SREBP) that are characteristic of a higher risk of genetic diseases in humans such as hyperchlolesterolemia. The corresponding polymorphisms, especially the polymorphisms on SREBP-1 and SREBP-2 are frequently observed in Alzheimer patients (SREBP-2). They are also characterized by a specific behavior in the therapy of HIV patients with proteas inhibitors and appear to have an influence on the mortality.

4 Claims, 4 Drawing Sheets

SREBP-1 Polymorphism (mmol/L)

SREBP-2 Polymorphism (mmol/L)

DNA POLYMORPHISMS IN STEROL REGULATOR ELEMENT BINDING PROTEINS

CROSS REFERENCES TO RELATED APPLICATIONS

This application claims the priority of Swiss patent application 1277/99, filed Jul. 9, 1999, the disclosure of which is incorporated herein by reference in its entirety.

TECHNICAL FIELD

The present invention relates to polymorphisms, in particular deoxyribonucleic acids (DNA or DNS)-polymorphisms, in Sterol-Regulator Element-Binding Proteins, in particular protein-1 (SREBP-1) and protein-2 (SREBP-2) or the use of said polymorphisms for diagnosis, respectively, but as well for active compound screening.

BACKGROUND ART

In the last decades, epidemiological long term studies have identified numerous factors accelerating formation of atherosclerosis and thereby promoting development of cardiac infarctions. Despite of avoiding risk factors and of behavior increasing the risk of atherosclerosis, the development of pronounced atherosclerotic changes culminating in heart infarction can even be observed in young adults. In such cases, genetic factors play a decisive role. It is for example known that defects of genes playing an important role in cholesterol metabolism require medication with cholesterol lowering drugs. The early detection of a genetic defect allows that counter measures can be taken in time.

Therefore, it is desirable both from a diagnostic point of view and from a therapeutical point of view to be able to recognize and to detect crucial genetic alterations (see A. R. Miserez, Die Bedeutung genetischer Faktoren bei der Entstehung des Herzinfarkts, uni nova, April 1998, S. 44–52).

Cholesterol, besides being the precursor of steroid hormones and bile acids, is an essential constituent of the cell membrane decisively enhancing its permeability-barrier properties. Human cells control their intracellular cholesterol concentration tightly by regulating the receptor-mediated uptake of extracellular cholesterol-containing low density lipoproteins (LDL) and the intracellular cholesterol biosynthesis. LDL particles bind to the LDL receptor (LDLR) by their apolipoprotein (apo) B moieties. The binding and subsequent internalization of these lipoprotein-receptor complexes can be partially or completely abolished if one of the proteins involved in this process is defective or missing. Mutations of the genes encoding the apolipoprotein E (causing familial dysbetalipoproteinemia (FDL)), the apo B-100 (causing familial defective apo B (FDB)), and the LDL receptor (causing familial hypercholesterolemia (FH)) lead to an accumulation of cholesterol-containing particles in the plasma, which is associated with an increased risk of coronary artery disease. In most of the tested populations, said mutations can only explain 4.2 to 7% of cases with hypercholesterolemia (defined as the 10% of persons of a population with LDLC concentrations above the ninetieth percentile). Thus, the casual gene defects for the majority of affected people with increased plasma LDLC are not yet identified.

The promoters of the LDLR gene and of the genes involved in the cholesterol biosynthesis including the hydroxymethylglutaryl (HMG) CoA synthase, farnesyl-pyrophosphate synthase, and squalene synthase genes, contain specific nucleotide sequences, so-called sterol regulatory elements (SREs).

It is already known that two proteins, SRE-binding protein-(SREBP-) 1 and SREBP-2, bind the SREs in the promoters of these genes and activate their transcription rates. When cells are deprived of sterols, both proteins are activated by two proteolytic steps, first by a sterol-sensitive, and then by a cholesterol-independent step. These cleavage events release 68 kDa peptides from the $NH_2$-terminal region of the SREBP-1 and -2 precursor proteins in the cytoplasm. The $NH_2$-terminal, mature form of the transcription factors enters the nucleus and binds the SREs in the promoters of cholesterol-regulating genes. As a consequence, these genes are activated, thus leading to an increase in the receptor-mediated uptake of LDL as well as to an enhanced intracellular cholesterol biosynthesis.

When cholesterol accumulates in the cell, the first, cholesterol-sensitive cleavage event is inhibited, the mature forms of the SREBPs disappear and transcription rates decline, thereby preventing excessive accumulation of cholesterol in the cell. SREBP-1 and SREBP-2 regulate numerous SRE-containing genes involved in cholesterol homeostasis. In addition, SREBP-1 activates the HMG CoA reductase and the squalene synthase. SREBP-1 and SREBP-2 are members of the so-called basic helix-loop-helix leucine zipper transcription factor family. The genes encoding these factors have been cloned recently, and their genetic structures have been characterized (20,21).

Despite of the available knowledge, the percentage—as mentioned above—of identifiable risk patients for e.g. hypercholesterolemia is below 7%.

Therefore, the present invention had the aim to improve the early diagnosis and therapy of risk patients.

Said aim is achieved by providing diagnostic methods as well as polymorphisms in the SREBP genes which are suitable for the use in said diagnostic methods, in particular polymorphisms which are found in a fraction of patients with altered lipid metabolism, in particular cholesterol metabolism, preferably in a big fraction of such patients.

DISCLOSURE OF THE INVENTION

Hence, it is a general object of the invention to provide a method for the detection of an increased or reduced disease risk and/or mortality risk and/or an increased or reduced sensitivity to therapeutical methods or side effects, respectively.

Further objects of the present invention are the use of polymorphisms for diagnosis, for the evaluation of disease treatments and for drug screening as well as the provision of suitable polymorphisms.

It was surprisingly found that polymorphisms in sterol-regulator element binding proteins (SREBP), in particular SREBP-1 and SREBP-2, are indicators for health risks or therapy risks, respectively. The method according to the invention is characterized in that after having taken a blood or tissue sample, respectively, said blood or tissue sample, respectively, is examined for the presence of a polymorphism in at least one SREBP wherein the presence of a polymorphism can be determined on nucleic acid level and/or protein level. The term polymorphism as used herein describes each naturally occurring sequence variation in humans, preferably a sequence variation found in a big percentage of the population.

In a preferred method nucleic acid sequences having a characteristic polymorphism, in particular a polymorphism of SREBP-1 and/or SREBP-2, are used on a DNA and/or RNA chip, so called microarray (DNA chip) technology. Other methods are e.g. PCR followed by a restriction digestion, e.g. with MspI or XmnI, respectively; single stranded conformation polymorphism (SSCP) method, denaturing gradient gel electrophoresis (DGGE) method; protein truncation test (PTT); restriction fragment length polymorphism (RFLP) method; Cleavage fragment length polymorphism (CFLP) method; chemical cleavage of mismatches method; sequencing, minisequencing (snap shot sequencing); methods based on high pressure liquid chromatography (HPLC) (dHPLC); methods based on mass spectroscopy; dot blot methods (allele specific oligonucleotides): allele specific PCR methods (allele specific oligonucleotides); real time quantitative PCR spectrophotometry (e.g. TaqMan™, Light Cycler™); and luminescent non-gel based molecular interrogation.

The polymorphisms which are in the scope of the present invention of special interest, in particular polymorphisms found in the SREBP-1 and SREBP-2 genes, are associated with an altered protein function. The presence of mutations in the SREBP-1 and SREBP-2 gene which are below further described leads e.g. to an improved or reduced activation of the LDL receptor resulting in an altered cholesterol level in humans.

In the scope of the present invention it was further found that corresponding polymorphisms are indicators for an increased or reduced disease risk, in particular for an increased or reduced risk, respectively, to become affected of hypercholesterolemia or Alheimer's disease. Said polymorphisms allow also an evaluation of the risk for the occurrence of problems associated with HIV therapy, in particular the therapy with protease inhibitors and allow a risk assessment for the development of any disease associated with an increased mortality risk, independently of an optionally associated cholesterol modification or Alzheimer's disease.

The invention is further described below and by the figures.

MODES FOR CARRYING OUT THE INVENTION

Polymorphisms in the SREBP genes can generally be detected as described below for the SREBP-1 and SREBP-2 genes.

The special polymorphisms can e.g. be detected by designing oligonucleotides corresponding to the intron sequences of SREBP-1 and SREBP-2 genes which are directly adjacent to the exon/intron boundary and by testing both genes for sequence variations using the single stranded conformation polymorphism method.

In this way the following relative often occurring polymorphisms were found. Each of said polymorphisms is compared to the normal gene wherein NS refers to the nucleic acid sequence and AS refers to the amino acid sequence:

SREBP-1 (wildtype):

```
NS  G CAC CTA GGC AAA GGC TTC  (Seq. Id. No. 1)
AS    H   L   G   K   G   F    (Seq. Id. No. 2)
```

SREBP-1-exon 18c-polymorphism (SREBP-1-G1028G or SREBP-1c-G1028G):

```
NS  G CAC CTA GGG AAA GGC TTC  (Seq. Id. No. 3)
AS    H   L   G   K   G   F    (Seq. Id. No. 4)
```

SREBP-2 (wildtype):

```
NS  CT GCT GCC GCC AAC CTA CA  (Seq. Id. No. 5)
AS   A   A   A   N   L   Q     (Seq. Id. No. 6)
```

SREBP-2-exon 10-polymorphism (SREBP-2-A595G):

```
NS  CT GCT GCC GGC AAC CTA CA  (Seq. Id. No. 7)
AS   A   A   G   N   L   Q     (Seq. Id. No. 8)
```

In the same manner, a further polymorphism with a relative high incidence was found which in the meantime was published in the context of a diploma thesis (see diploma thesis done at the department of research, university hospitals Basel, by Patrick Y. Müller, "Sterol regulatory element binding protein 2: . . . ") and which subsequently was designated SREBP-2-exon-6-polymorphism or SREBP-2-R371K.

A comparison of the wildtype sequence to said further polymorphism shows a substitution at the protein level, namely mutation of an arginine (R) to a lysine (K) at position 371 (R371K) in exon 6, namely:

SREBP-2 (wildtype):

```
NS       CTG AGG AAG
AS        L   R   K
```

SREBP-2-exon 6-polymorphism (SREBP-2-R371K):

```
NS      CTG AAG AAG
AS       L   K   K
```

Figure 1A:
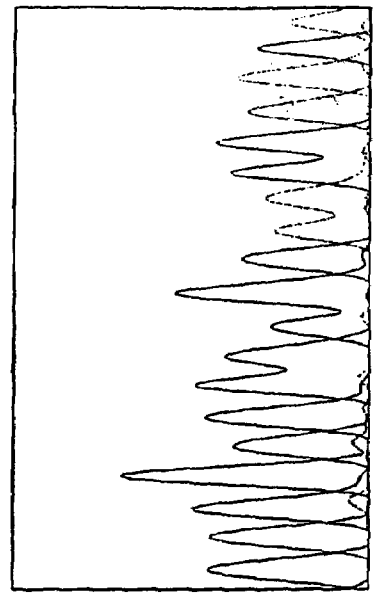
FIG. 1A shows a chromatogram for the identification of the exon polymorphism in SREBP-1, and the detected polymorphism, namely a mutation in the SREBP-1 gene (exon 18c) at amino acid position 1028 (G1028G) which does not lead to an amino acid substitution but generates a Xmn I restriction site.
Figure 1B:
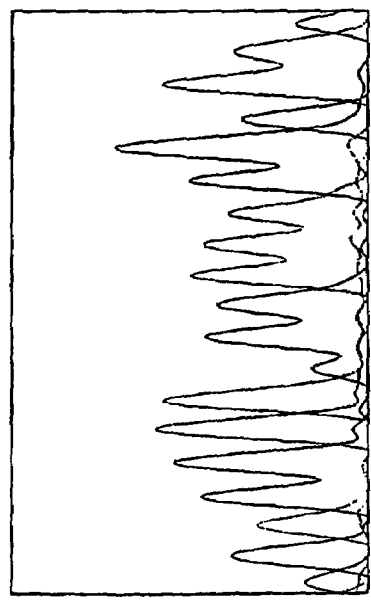
FIG. 1B shows a chromatogram for the identification of the exon polymorphism in SREBP-2, and the detected polymorphism, namely a mutation in the SREBP-2 gene (exon 10) at amino acid position 595 (A595G) which leads to an amino acid substitution (alanine to glycine) and additionally generates a MspI restriction site.
Figure 2B:
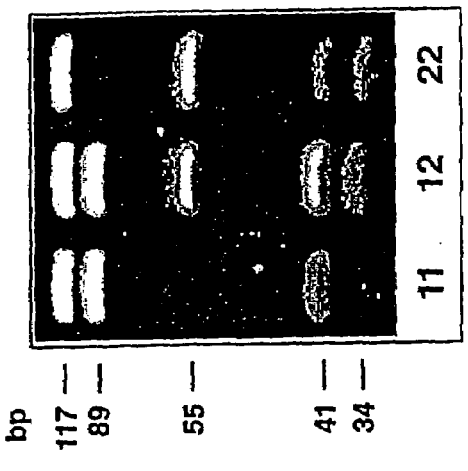
FIG. 2B shows how homozygous and heterozygous carriers of the corresponding mutation can be identified by large scale screening of large person groups by means of PCR amplification of the whole 5' end of exon 10 (SREBP-2) and subsequent restriction enzyme digestion.
Figure 2B:
Figure 2B:
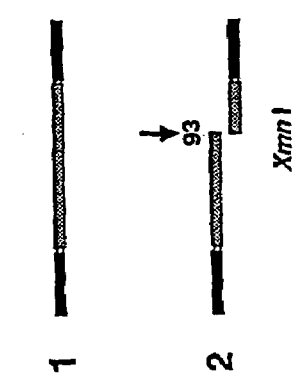
Figure 2A:
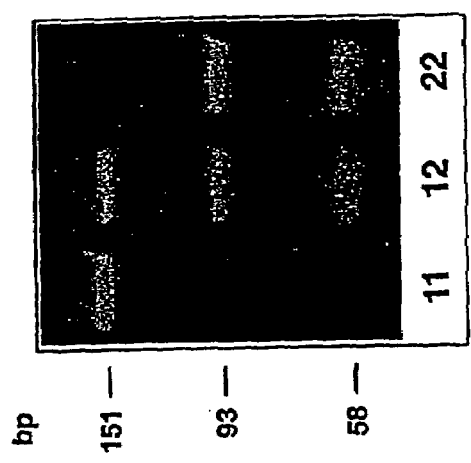
FIG. 2A shows how homozygous and heterozygous carriers of the corresponding mutation can be identified by large scale screening of large person groups by means of PCR amplification of the whole exon 18c (SREBP-1) and subsequent restriction enzyme digestion.

As can be seen from the above sequences, each of said polymorphisms has an altered nucleic acid in the exon range wherein only two of said three polymorphisms, namely those of SREBP-2, have a mutation which is detectable at the protein level (see FIG. 1A, FIG. 1B). But all three polymorphisms generate new cleavage sites for restriction enzymes, namely in SREBP-1 a cleavage site for XmnI and in SRBEP-2 a cleavage site for MspI or DdeI, respectively.

It is obvious that said polymorphisms are as well present in the complementary strands so that any reference throughout this application to nucleotide sequences comprises the corresponding disclosure of said complementary sequences.

The finding that the polymorphism in the SREBP-1 gene does not lead to an alteration at the protein level but nevertheless can be correlated with the incidence of hypercholesterolemia strongly suggests that said polymorphism is associated with one or several mutation in the same gene or has an influence at the RNA level. Said hypothesis is in agreement with the fact that said polymorphism in the SREBP-1 gene not only is associated with the incidence of hypercholesterolemia but at the same time is associated in HIV patients with a deficiency to increase the total cholesterol concentration and triglyceride concentration after administration of protease inhibitors. Therefore, said polymorphism is a valuable tool for the risk assessment for the incidence of undesired effects and cessation of a treatment with protease inhibitors.

Another valuable feature of the described polymorphisms, in particular of the SREBP-2-A595G-polymorphism, is its prevalence in patients with Alzheimer's disease in comparison with its presence in the population in general, namely 7% in patients with Alzheimer's disease compared to 2.4% in the population in general.

Furthermore, it was surprisingly found that all three polymorphisms which are further described above have a significant influence on the mortality of its carrier.

It can be summarized that SREBP-2-A595G is particularly suitable to make a statement concerning the risk for a general cholesterol increase whereas SREBP-1c-G1028G is particularly suitable as a prognostic marker for the individual reaction (risk for cholesterol increase) after administration of medicaments. For statements concerning the risk of developing Alzheimer's disease (also independent of an optionally associated cholesterol increase or cholesterol reduction) SREBP-2-A595G is preferred while for the determination of the risk for the development of a disease which is associated with a higher mortality risk (also independent of an optionally associated cholesterol modification or Alzheimer's disease) all three above further described polymorphisms are suitable whereby SREBP-2-A595G and SREBP-1c-G1028G are preferred.

While polymorphisms of SREBP are in general suitable for the method, SREBP-1 polymorphisms and/or SREBP-2 polymorphisms are preferred, in particular polymorphisms leading to an increased or reduced activation of genes of the lipid metabolism, in particular of the cholesterol metabolism. Polymorphisms leading to a increased or reduced plasma concentration of at least one lipid, in particular cholesterol, are more preferred.

It was found that a polymorphism having a recognition site for a cleavage site which lies within the polymorphism is particularly suitable for a method using said recognition sequence. Such recognition sites are e.g. the recognition sequence for XmnI or MspI, i.e. GAANNNNTTC or CCGG, wherein N can be any nucleotide. Sequences comprising such recognition sequences are e.g.

SREBP-1, exon 18c: GCACCTAGGGAAAGGCTTC, (Seq. Id. No. 3) and

SREBP-2, exon 10: CTGCTGCCGGCAACCTACA (Seq. Id. No. 7).

Said sequences either alone or together with further nucleotides of their natural vicinity can e.g. be used as probes. In addition there are further suitable sequences such as the following nucleic acid sequence, optionally together with further nucleotides of the natural vicinity of said sequence, namely SREBP-2, exon 6: CTGAAGAAG.

A preferred method at nucleic acid level is characterized in that after having taken blood or a tissue sample, respectively, and after DNA extraction at least part of a sequence, in particular of an exon, of a SREBP comprising a polymorphism is amplified using two oligonucleotides wherein said polymorphism is characteristic for an increased or reduced activation of genes of the lipid metabolism, in particular cholesterol metabolism, and particularly preferred for an increased or reduced risk for hypercholesterolemia in humans, and that the product of said amplification is subjected to a digestion with a suitable restriction enzyme or subjected to denaturation and that the product of the digestion or the product of the denaturation, respectively, is electrophoretically separated.

If the polymorphism lies in a exon, preferably at least one of the oligonucleotide sequences lies in the intron range which is adjacent to the exon where the polymorphism is found such as e.g. the pairs S1.18cF (Seq. Id. No. 9): 5'-TTATT-TATAATCTGGGTTTTGTGTC-3' and S1.18cR (Seq. Id. No. 10): 5'-GGGAAGAGCTAAGT-TAAAAGTTGTG-3' or EcoR I.S1.18cF (Seq. Id. No. 11): 5'-CGGAATTCT-GAAATTATTTATAATCTGGGTTTTGTGTC-3' and EcoR I.S1.18cR (Seq. Id. No. 12): 5'-CGGAAT-TCATCGGGGAAGAGCTAAGTTAAAAGTTGTG-3' or S2.10P.F (Seq. Id. No. 13): 5'-GCCAGTGACCATTAA-CACCTTTTGA-3' and S2.10P.R. (Seq. Id. No. 14): 5'1-TCGTCTTCAAAGC-CTGCCTCAGTGGCTGGC-3' or EcoRI S2.10F (Seq. Id. No. 15): 5'1-CGGAATTCGC-CAGTGACCATTAACACCTTTTGA-3' and EcoRI S2.10R (Seq. Id. No. 16): 5'1-CGGAATTCTG-CAGCAAGCCAGTCATCAGCAGCT-3'

EcoRI S2.6F (Seq. Id. No. 17): 5'-CGGAATTCTGGTCT-CACTGTGTTTTCACTCATC-3'

EcoRI S2.6R (Seq. Id. No. 18): 5'-CGGAATTCGC-CAGGGCTGACAAGCCTTTTCTCA-3'.

Besides the above mentioned sequences or sequence pairs, respectively, other sequences or sequence pairs, respectively, can be used such as sequences hybridising to the above mentioned sequences under stringent conditions, including sequences without or with other recognition sequences, respectively, than the above indicated EcoRI sequence. The total length of such sequences is usually 15 to 30 bases.

Suitable polymorphisms can be found by amplifying and analyzing a SREBP sequence of interest, comparing the exon regions of said sequence of interest to the exon regions of the type of sequence of the corresponding SREBP which is most often found in a population and examining sequences with found differences for dysfunction, whereby preferably the differences lead to a different amino acid and/or in particular to an recognition site for a restriction enzyme. Such a recognition site lies preferably in a exon but said recognition site can as well lie in an intron and e.g. lead to a splice variant.

The big influence of the found polymorphisms on factors influencing various diseases is below discussed by means of the more often occurring polymorphisms A595G and G1028G:

Mutation A595G in the SREBP-2 gene is not associated with a significant modification of the mean plasma cholesterol concentration. The amino acid sequence corresponding to the published cDNA sequence (12,15,16) was defined as wildtype, although—at least in the examined Swiss collective—the sequence coding for glycine at position 595 had a much higher prevalence than the published alanine at this position. More than 93% of all individuals were heterozygous or homozygous carriers of mutation A595G. Both genes were sequenced from a cDNA library deriving from HeLa cells stemming from a carcinoma of an afro-american woman (Henriette Lacks) (17). Direct experiments with HeLa cells showed that said cells were homozygous with regard to the non-mutated A595G genotype and indicated that said person was a homozygous carrier of the wildtype alles—a condition which was only found in 6.69% of the Swiss inhabitants collective. The observation of a high prevalence of mutation A595G led in the scope of the present invention to the hypothesis that the rare wildtype in homozygous form (11) is associated with a higher plasma cholesterol concentration and that the non-mutated form (22) is associated with a lower concentration that thus an autosomal-recessive effect could exist and that therefore allele combination 11 and 12/22 were compared to each other.

The sample of enrolled individuals was heterogeneous with regard to the plasma cholesterol concentration which was in the range of 1.95 to 22.65 mmol/l. Said large range can be explained by the inclusion of random sampling but as well by inclusion of selected collectives and therefore normocholesterolemic and hypercholesterolemic individuals. It was therefore not surprising that without stratification of the sample in random/non-random selected or in normocholesterolemic/hypercholesterolemic subgroups, the effect of at least one of the polymorphisms, polymorphism G1028G, did not achieve statistical significance (P=0777). Similarly, for mutation A595G the probability that differences of the plasma cholesterol concentrations between the allele combination 11 compared to $^{12}\!/_{22}$ is by chance was reduced from P=0.0003 (unpaired t-Test, no stratification) to P<0.0001 (analysis of variance=ANOVA, stratification).

Figure 3:
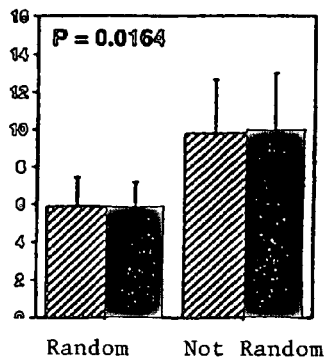
FIG. 3 shows for SREBP-1 and SREBP-2 the His 20 comparison between carriers and non-carriers of the polymorphisms with regard to the corresponding, average total cholesterol concentration and the gene—gene interaction with apolipoprotein E-gene.
Figure 3:
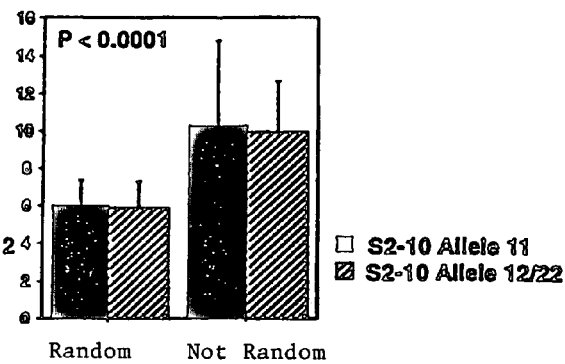
Figure 3:
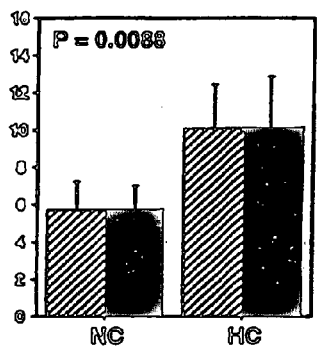
Figure 3:
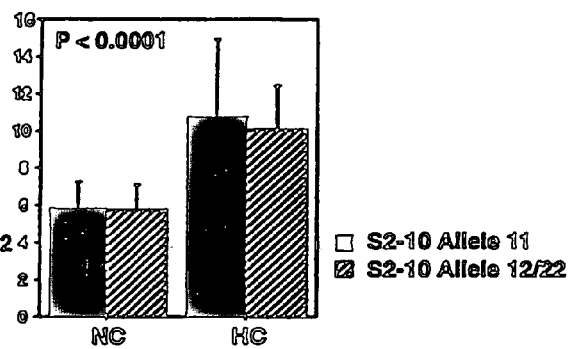
Figure 3:
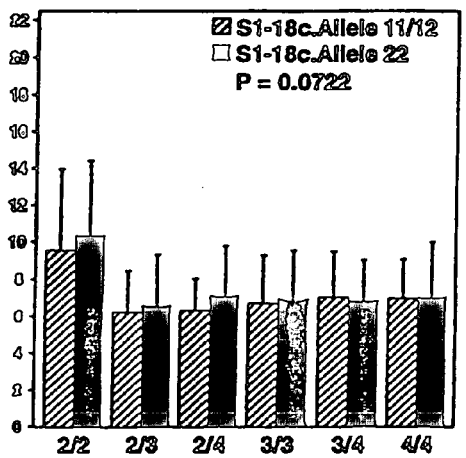
Figure 3:
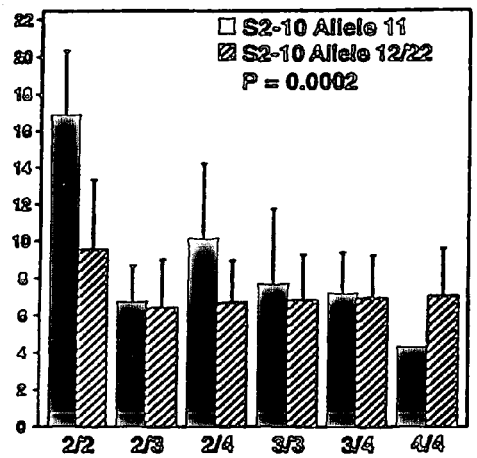

Moreover, for both polymorphisms the associations between a defined allele combination and higher plasma cholesterol concentrations (allele combination 22 of polymorphism G1028G, allele combination 11 of polymorphism A595G; depicted in black in FIG. 3, E and F) were stronger in presence of polymorphism R158C ($\epsilon$2 phenotype) and were weaker in absence of polymorphism C112R (($\epsilon$4 phenotype) in the apo E gene. It was found that said gene—gene interactions clearly influence the association of polymorphism G1028G (allele combination 22) with higher plasma cholesterol concentrations: after exclusion of the carriers of mutation C112R the effect of mutation G1028G→G in homozygous form (22) was highly significant (P=0.0002).

It was therefore possible to show that both SREBP genes modify plasma cholesterol concentrations in humans similarly to the known effects of both polymorphisms in the apo E gene (C112R and R518C). Furthermore, gene—gene interactions became obvious when SREBP-1 and SREBP-2 gene polymorphisms were correlated with the polymorphisms of the apo E gene.

The plasma triglyceride levels were elevated in 11.6% of the individuals with secondary hyperlipoproteinemia. An effect of elevated triglyceride concentrations is underlined by the fact that, if individuals with elevated triglyceride concentrations were excluded, mutation A595G had a significant effect on male individuals with diabetes mellitus (P=0.0018), but said effect was not observed when individuals with elevated triglyceride concentrations were included.

Mutation A595G in the SREBP-2 gene could be closely correlated both with another mutation and directly affect the cleavage rate of the protein. Though exon 10 where mutation A595G is localized does not belong to the part of the mature protein that migrates to the cell nucleus. Nevertheless, said part of the protein is connected with the activity of the protein by influencing the cleavage reactions which activate the precursor of SREBP-2.

Proteolysis is initiated by a protein recognizing a highly conserved RXXL sequence of the SREBP precursors which is localized in the hydrophilic loop. The first proteolysis step separates the $NH_2$-terminal domain and the COOH-terminal domain. After said first sterol sensitive step, the remaining membrane bound $NH_2$ terminal fragment is released by a second sterol independent step. Said second proteolysis step (site 2) is localized within the membrane spanning region and is mediated by the site-2 enzyme. Said second step only occurs when site-1 proteolysis has occurred. However, a precondition for site-1 proteolysis is the formation of a complex of SREBP and the so called SREBP cleavage activating protein (SCAP). When the sterol level is low in cells, said protein binds to the COOH terminal domain. The formation of the SREBP-SCAP complex is crucial for the site-1 proteolysis step and is dependent on the integrity of the COOH terminal domain of SREBP-2 and SCAP (18,19). On the basis of experiments recently performed by Sakai et al. (18) which identified the C-terminal part of SREBP precursors as regulatory unit, the mutation in said domain which causes a significant reduction of the average plasma cholesterol concentration, raises the question of a slightly facilitated formation of the SREBP-SCAP complex when mutation A595G is present.

The effect of polymorphism G1028G seems to be influenced by the gene—gene interactions with the apo E gene. In contrary to mutation G1028G in the SREBP-1 gene, mutation A595G in the SERBP-2 gene has as marker significant effects on the plasma cholesterol concentrations both when the whole collective is examined and when the different subgroups are analyzed. It is probable that the mutation shows its effect by directly influencing the cleavage reaction which is responsible for the sterol dependent activation of SREBP-2.

From the above comment ensues that both genes significantly modify the individual plasma cholesterol concentrations. Although many genes play a role in the intracellular and extracellular cholesterol metabolism, until now only the apo E gene as modifying gene has been of bigger use with regard to the general population. Other genes involved in the lipoprotein metabolism such as the LDL receptor gene, the apo B-100 gene or a further unknown gene on chromosome 1p34.1-p32 could have a significant effect on plasma cholesterol concentrations in their mutated state. However, said mutations are very seldom compared to the polymorphisms in the apo E gene and the polymorphisms in the SREBP-1 gene and SREBP-2 gene which were now discovered. Even mutation R3'500Q which has so far the highest observed prevalence with 209 affected individuals of the general population (in Switzerland) does not occur often enough in order to examine the influence of a defined gene on the cholesterol metabolism of the general population using said polymorphism.

The methods and polymorphisms of the present invention are therefore very valuable tools for the early detection of risk patients as well as for the optimization of prophylaxis and therapy. Furthermore, said polymorphisms are suitable targets for drug screening as well as the evaluation of a therapy for a disease such as e.g. HIV. The value of the preferred polymorphisms of the present invention is also the presence of recognition sites in closest proximity to the polymorphism. Said recognition sequences are in SREBP-1 the recognition sequence for XmnI, namely GAANNNNTTC, wherein N can be any desired nucleotide and in SREBP-2 the recognition sequence for MspI i.e. CCGG.

The present invention relates also to a method for the detection of risk carriers as well as to means for said methods such as oligonucleotide sequences for the amplification of DNA regions of interest.

A preferred method for the detection of risk carriers is characterized by the following steps.
1. Taking a blood or tissue sample
2. DNA extraction
3. Amplification with suitable primers
4. Digestion with suitable restriction enzymes or denaturation of the PCR products
5. Electrophoretical separation with a suitable gel In particular the polymorphisms of special interest are detected by means of digestion with suitable restriction enzymes and further mutations can be found by means of denaturation (single stranded conformation polymorphism=SSCP).

A preferred oligonucleotide sequence for the amplification of a DNA region which corresponds to an exon region where a polymorphism is found, is characterized in that said oligonucleotide sequence lies in an intron region which is adjacent to the exon where the polymorphism exists and close to the exon/intron boundary or lies in the exon provided that thereby the number of cleavage sites is reduced.

Preferred oligonucleotides for the SREBP-1 polymorphism are the oligonucleotides S1.18cF (Seq. Id. No. 9): 5'-TTATTTATAATCTGGGTTTTGTGTC-3' and S1.18cR (Seq. Id. No. 10): 5'-GGGAAGAGCTAAGTTAAAAGT-TGTG-3', which allow the detection of splice variants, as well as oligonucleotides, which further comprise additional EcoR I-cleavage sites such as EcoR I.S1.18cF (Seq. Id. No. 11): 5'-CGGAATTCTGAAATTATT-TATAATCTGGGTTTTGTGTC-3' and EcoR I.S1.18cR (Seq. Id. No. 12): 5'-CGGAATTCATCGGGGAA-GAGCTAAGTTAAAAGTTGTG-3'. In order to amplify exon 10 inclusive its exon/intron border the oligonucleotides S2.10P.F (Seq. Id. No. 13):5'-GCCAGTGACCATTAA-CACCTTTTGA-3' and S2.10P.R (Seq. Id. No. 14):5'-TCGTCTTCAAAGCCTGCCTCAGTGGCTGGC-3' or EcoRI S2.10F (Seq. Id. No. 15): 5'-CGGAATTCGCCAGT-GACCATTAACACCTTTTGA-3' and EcoRI S2.10R (Seq. Id. No. 16): 5'-CGGAATTCTGCAGCAAGCCAGTCAT-CAGCAGCT-3' are preferred.

A particular use of SREBP polymorphisms relates to their application in so called DNA or gene chips. Methods using said chips which allow the simultaneous detection of various gene defects are described in the literature. There is information material from the company Affymetrix concerning their GeneChip™ systems but there are as well publications in scientific journals such as the publication of Mark Chee et al., Accessing Genetic Information with High-density DNA Arrays, Science Vol. 274, p. 610–4, (1996) and David G. Wang, Large scale Identification, Mapping, and Genotyping of Single nucleotide polymorphisms in the human Genome, Science Vol. 280, p. 1077–82, (1998).

The method can briefly be summarized as follows: By means of photo lithography defined areas of a wafer are fed stepwise to the chemical synthesis of single stranded DNA or RNA wherein the protective film is renewed after each synthesis step followed by the selective removal of said protective film from sites where a defined nucleotide should be added. This procedure allows the production of areas which are selective for defined polymorphisms. Common labels can be used for the visualization of hybridization with target sequences e.g. light emitting labels such as e.g. biotinylation and detection with streptavidin or fluorescence labels.

By means of removal of labeled non-hybridized fragments hybridisations are directly visible or after a further treatment. It is self-evident that the single steps of the method can be varied e.g. with regard to the time point of labeling or the kind of labeling. This kind of variations are known to a man skilled in the art.

A chip which is suitable for the early detection of patients with an increased risk for hypercholesterolemia comprises besides the normal SREBP-1 and SERBP-2 sequences the corresponding polymorphisms which are an object of the present invention. It is obvious that besides said SREBP-1 and SREBP-2 means for analysis also the corresponding sequences for further polymorphisms which are characteristic for hypercholesterolemia i.e. FH, FDB and FDL can be present.

It is obvious that a corresponding chip can also be used for the diagnosis of other diseases which show a dependency on SREBP-1 and/or SREBP-2 such as Alzheimer's disease or said chip can be constructed for the diagnosis of several diseases or risk factors by fixing polymorphisms characteristic for the diseases or risks of interest to said chip. Sequences of interest are e.g. for the studies of cardiovascular risks, sequences of the following group (preferred sequences are underlined):

11β-Hydroxylase Aldosteron-Synthase Gene, 11-Hydroxysteroid-Dehydrogenase (HSD11K)Gene, 17αHydroxylase (CYP17A)Gene, 3-Hydroxy-3-Methylglutaryl (HMG)Coenzyme A Reduktase Gene, 3-Hydroxy-3-Methylglutaryl (HMG)Coenzyme A Synthase Gene, Acyl Coenzyme A:diacylglycerol acyltransferase Gene, Acyl-Coenzyme A:cholesterol acyltransferase (ACAT)-1 Gene, Alpha-1-Antichymotrypsin Gene, Alpha-1-trypsin Gene, Alpha-Glaktosidase A Gene, Alpha-L-Iduronidase (IDUA) Gene, Alpha-Lecithin cholesterol acyltransferase (LCAT) Gene, Alpha-Synuclein Gene, Angiotensin Gene, Angiotensin II Typ 1 Rezeptor Gene, Angiotensin-converting Enzym Gene, Anti-trypsin Gene, Apolipoprotein (a) Gene, Apolipoprotein AI-CIII-AIV Gene cluster, Apolipoprotein B-100 Gene, Apolipoprotein CI Gene, Apolipoprotein E (epsilon 2), Apolipoprotein E (epsilon 4), Apolipoprotein E Gene, Apolipoprotein E Rezeptor 2 Gene, Benzodiazepine Receptor Gene, CD-36 Gene, Cholesterol 24-Hydroxylase Gene, Cholesteryl ester transfer Protein (CETP) Gene, Cystathionin-β-Synthase Gene, Cystatin C Gene, Cytochrome P450 cholesterol side-chain cleavage Enzyme Gene, Epithelial $Na^+$-channel (β-subunit) Gene, Farnesyl-Pyrophosphate (PP) Synthase Gene, Fibrinogen Gene, Glucokinase Gene, GLUT1 Glucose Transporter Gene, Hepatic Lipase Gene, High density lipoprotein (HDL) Receptor Gene, Homogentisinacid-Oxidase Gene, Hormone-sensitive Lipase Gene, Iduronat-2-Sulfatase Gene, Interleukin-8 Gene, Lecithin cholesterol acyltransferase (LCAT) Gene, Lipooxygenase Gene, Lipoprotein Lipase Gene, Low density lipoprotein receptor-related Protein (LRP) Gene, Low density lipoprotein Receptor Gene, Lysosomale acid Lipase Gene, Macrophage Scavenger Receptor (SR-A) Gene, Macrophage Scavenger Receptor (SR-BI) Gene, Methylene-tetrahydrofolate Reduktase Gene, Microsomal triglyceride transfer Protein (MTP) Gene, NF-$_K$B Gene, Niemann-Pick C1 Protein Gene, Oxysterol binding Protein (OSBP) Gene, Paraoxonase-1 Gene, Paraoxonase-2 Gene, Peroxisome proliferator-activated receptor (PPAR) alpha Gene, Peroxisome proliferator-activated receptor (PPAR) beta Gene, Peroxisome proliferator-activated receptor (PPAR) gamma Gene, Plasminogen activator-inhibitor-1 Gene, Site-1 Protein (S1P) Gene, Site-2 Protein (S2P) Gene, Squalene Synthase Gene, SREBP cleavage-activating Protein (SCAP) Gene, Steroid acute regulatory Protein (StAR) Gene, Steroid-11β-Hydroxylase (CYP11B1) Gene, Sterol-27-Hydroxylase Gene, Sterol regulatory element-binding protein (SREBP)-1a Gene, Sterol regulatory element-binding protein (SREBP)-1c Gene, Sterol regulatory element-binding protein (SREBP)-2 Gene, Very low density lipoprotein (VLDL) Receptor Gene.

For the studies of neurological risks for example a chip comprising sequences of the below mentioned group is suitable (preferred sequences are underlined):

A-beta precursor Gene, Adenosine monophosphate deaminase Gene, Alpha 2-monoglobulin Gene, Alpha-1-Antichymotrypsin Gene, Alpha-1-trypsin Gene, Alpha-2 Macroglobulin Gene, Alpha-ketoglyterate dehydrogenase Gene, Amyloid beta-protein precursor Gene, Amyloid precursor Protein Gene, Amyloid precursor-like Protein 1 Gene, Amyloid precursor-like Protein 2 Gene, Antitrypsin Gene, Apolipoprotein (a) Gene, Apoliprotein AI-CIII-AIV Gene cluster, Apolipoprotein E (epsilon 2), Apolipoprotein E (epsilon 4), Apolipoprotein E Gene, Apolipoprotein E Receptor 2 Gene, Bcl-2 Gene, Beta-amyloid precursor Protein Gene, Beta-nerve growth factor Gene, Calbindin-D Gene, Captase Gene, Cathepsin D Gene, CD36 Gene, Clusterin Gene, Cyclooxygenase-2 Gene, Cystatin C Gene, Cytochrome C Oxidase 1 Gene, Cytochrome C Oxidase 2 Gene, Cytochrome Oxidase Gene, Dihydrofolate Reduktase Gene, Dihydrolipoylsuccinyltransferase (DLST) Gene, Endopeptidase 1 Gene, Estrogen-Bcl xL Gene, Fe65L2 Gene, Gamma-synuclein Gene, Gelsolin Gene, GLUT1 Glukose Transporter Gene, GLUT4 Glucose Transporter Gene, Glutaminacid Decarboxylase Gene, Glutation S-transferase Gene, HLA-A2 Gene, Interleukin-1 Gene, Interleukin-6 Gene, Interleukin-8 Gene, L-3-Hydroxyacyl-Coenzym A Dehydrogenase Gene, Lipooxygenase Gene, Low density lipoprotein receptor-related Protein (LRP) Gene, Low density lipoprotein Receptor Gene, Macrophage Scavenger Receptor (SR-A) Gene, Macrophage Scavenger Receptor (SR-BI) Gene, Methylene-tetrahydrofolate Reduktase Gene, Myeloperoxidase Gene, NF-$_K$B Gene, Niemann-Pick C1 Protein Gene, Non-A-beta component for amyloid (NAC) peptide Gene, Notch Gene, Ornithine transcarbamylase Gene, Presenilin 1 Gene, Presenilin 2 Gene, Prion Protein Gene (PRNP) Gene, Prostaglandin E2 Gene, Serotonin Gene, Serotonin Transporter Gene, Site-1 Protein (S1P) Gene, Site-2 Protein (S2P) Gene, SREBP cleavage-activating Protein (SCAP) Gene, Sterol regulatory element-binding protein (SREBP)-1a Gene, Sterol regulatory element-binding protein (SREBP)-1c Gene, Sterol regulatory element-binding protein (SREBP)-2 Gene, Superoxid dismutase gene, Tau (Protein) Gene, Very low density lipoprotein (VLDL) Receptor Gene, X11alpha Protein Gene, X11L2 Gene.

Furthermore, the polymorphisms, methods and chips of the present invention are also suitable to detect possible risk patients for the treatment with special medicaments such as a treatment with protease inhibitors in case of HIV infected individuals.

The present invention is now further illustrated by means of examples. It is to be distinctly understood that the invention is not limited to the examples described in the experimental part or limited to the explicitly mentioned embodiments therein, respectively.

Experimental Part

Preliminary Remarks

The polymorphisms were detected by synthesizing oligonucleotides to intron sequences of the exon/intron boundary so that also possible splice variants could be detected. Below the detailed procedure for the detection of relevant polymorphisms as well as their examination is described.

Subjects

A total of 3'078 subjects were enrolled in the study. DNA polymorphisms and rare mutations in five different genes were screened. In all groups of subjects, individuals with TC plasma concentrations below the $90^{th}$ percentile, standardized for age and gender, were classified as normocholesterolemic (NC); individuals with TC plasma concentrations above the $90^{th}$ percentile, as hypercholesterolemic (HC). 1'685 were enrolled from different, prospectively studied random samples. 630 individuals were collected from the "Swiss PREvalence for Apolipoprotein Defects" (SPREAD) study, a large, cross-sectional survey which included unrelated male individuals from the German, French, and Romansh speaking parts of Switzerland who had been recruited for military service. Another 324 individuals were enrolled from the "Inter-Disciplinary study on Aging" (IDA). Another 413 elderly individuals who had been collected because of a potential impairment of their memory function but not because of hypercholesterolemia were enrolled from the Basel Memory Clinics (BMC) as a further control sample. In addition, 318 affected and/or unaffected individuals were from the "Study to Investigate the molecular Basis of hypercholesterolemia in Switzerland in Hyperlipidemic Individuals by Pedigree analysis" (SIBSHIP), a substudy of the Swiss MED PED (Make Early Diagnosis—Prevent Early Death) program, the latter being a multinational program endorsed by the WHO. 871 individuals were from samples collected because of potential primary and secondary hyperlipoproteinemias. The molecular diagnosis was based on the identification of the underlying mutation (familial defective apo B (FDB), familial dysbetalipoproteinemia (FDL), familial hypercholesterolemia, diagnosed molecularly or by cosegregation analysis (FHM)). The clinical diagnosis of familial forms of hyperlipoproteinemia was based on total and/or LDL cholesterol levels above the $90^{th}$ percentile, and a family history with at least two further family members with hypercholesterolemia. Individuals from families with these characteristics and triglyceride levels <3.7 mmol/L and/or tendon xanthomas were classified as having familial hypercholesterolemia, clinically diagnosed (FHC). Families with individuals without xanthomas and triglyceride levels ≧3.7 mmol/L were classified as having familial combined hyperlipidemia (FCH).

A total of 298 subjects were from the "Study on the molecular basis of Triggers Activating a Rise in Triglycerides and cholesterol in Endocrinological and Renal Diseases" (STARTER). A sample of 130 individuals with biochemically confirmed diabetes mellitus (fasting plasma blood glucose >7.8 mmol/L) (DIA), 78 individuals with hypothyroidism, and 14 individuals with renal insufficiency (creatinin clearance <50 ml/min) (RIN) were also enrolled in the study.

In all subjects at least age, gender, and total cholesterol concentrations prior to therapy with lipid-lowering drugs, and the clinical or molecular biological diagnosis, respectively, were assessed. Except for the SPREAD study, subjects were, in addition, clinically extensively characterized. In the IDA, BMC, SIBSHIP and STARTER studies height, weight, body mass index, blood pressure, the presence or absence of the clinical signs of hypercholesterolemia (xanthomas, xanthelasms, and arcus lipoides) and signs and symptoms of coronary heart disease, cerebrovascular diseases, and peripheral artery disease, as well as biochemical parameters such as plasma concentrations of total cholesterol, LDL cholesterol, HDL cholesterol, triglycerides, and thyroid-stimulating hormone (TSH) were assessed. The documentation included also the personal history of coronary heart disease, cerebrovascular disease, and peripheral artery disease, thyroid disorders, diabetes mellitus, daily intake of alcohol, and cigarette smoking (pack years), and in the SIBSHIP and STARTER studies a detailed family history with additional lipoprotein analyses (e.g. lipoprotein(a) [Lp(a)], apolipoprotein B, etc.).

In all these subjects, samples were anonymized for further laboratory testing and analysis.

Materials

*Thermus aquaticus* DNA polymerase and deoxynucleotides were purchased from Perkin Elmer Cetus Corporation (Norwalk, Conn., USA), and from Qiagen (Milden, Germany). Restriction endonucleases were from New England Biolabs Inc. (Beverly, Mass., USA) and prestained protein molecular weight markers and DNA molecular weight markers were from Roche Diagnostics (Basel, Switzerland). The oligonucleotides used were synthesized by Microsynth Inc. (Balgach, Switzerland). DNA was amplified in 200 μl tubes using thermocyclers of Perkin Elmer (GeneAmp® PCR System 9700) and of Stratagene (RoboCycler® Gradient 96 Temperature Cycler, Stratagene, La Jolla, Calif., USA). Agarose was purchased from BioRad (Irvines, Calif., USA) and polyacrylamide (acrylamide: bisacrylamide 37.5:1) from Oncor Inc. (Gaithersburg, Md., USA). Precast GMA™ Wide Mini S-50 gels and Spreadex EL 300 Wide Mini S-100 gels were purchased from Elchrom Scientific (Cham, Switzerland). Precast gels for polyacrylamide gel electrophoresis (Ready Gels 10%) were obtained from BioRad. [α-$^{32}$P] dCTP and Hybond-C extra nitrocellulose membranes were obtained from Amersham International (Buckinghamshire, UK. DH5α bacteria and 1 kb DNA ladders were purchased from GIBCO BRL, Life Technologies (Paisley, UK). QIAmp 96 DNA blood kits, Genomic tip kits, QIAquick Extraction and PCR purification kits, QIAprep Spin Miniprep kits, and QIAGEN Plasmid Midi kits were from Qiagen.

Methods

Individuals enrolled were screened for two known DNA polymorphisms in the apo E gene both causing amino acid substitutions (C112R, R158C), for a highly prevalent DNA mutation in the Swiss population located in the apo B-100 gene causing an amino acid substitution (R3'500Q), for a novel DNA polymorphism in the SREBP-1 gene (G1028G) which does not lead to a amino acid substitution, and for a novel polymorphism in the SREBP-2 gene leading to an amino acid substitution (A595G). A subset of these subjects where further family members with hypercholesterolemia had been studied (SIBSHIP study), was tested for the presence of DNA restriction fragment length polymorphisms in the LDLR gene, which allowed us to perform cosegregation studies for confirmation of LDLR defects. Subjects from the SIBSHIP study were, in addition, systematically screened for mutations in the LDLR gene.

1. Lipoprotein Analyses

Fasting blood samples were taken from the subjects enrolled in the study. Lipid and lipoprotein analyses were performed at the Central Laboratory, University Clinics, Basel, except for a small subset of subjects from the SHIB-SHIP study with familial forms of hyperlipoproteinemias who had already been treated at study entry; in these cases a wash-out period could not be performed for ethical reasons. In this subset of patients, total cholesterol concentrations were determined at the Central Laboratory prior to the beginning of drug treatment, or pretreatment total cholesterol concentrations partly determined at other laboratories were obtained from their general practitioners and included into the analysis. LDL cholesterol (LDLC) was precipitated with heparin (Merck, Darmstadt, Germany) and subsequently calculated using the Friedewald formula. HDL cholesterol (HDLC) was precipitated by means of phosphotungstic acid and magnesium ions (Roche Diagnostics). Total cholesterol, LDLC, and HDLC plasma concentrations were measured by the enzymatic colorimetric cholesterol 4-aminophenazone (PAP) method (Roche Diagnostics) on a Hitachi analyzer model 737.

2. DNA Extraction Method

Total genomic DNA from the subjects enrolled in the study was extracted from white blood cells by the salting out method (1) with modifications as described previously (2), or by using the QIAmp™ 96 DNA Blood kits (Qiagen).

3. Single-Strand-Conformation Polymorphism (SSCP)

a) Radioactive Method

To screen for LDLR gene mutations, all 18 exons of the LDLR gene were amplified using oligonucleotides published by Hobbs et al. (3).

To amplify exon 18c of the SREBP-1 gene including its exon/intron boundaries allowing to detect splice site mutations as well, the following pair of oligonucleotides was used:

S1.18cF (Seq. Id. No. 9): 5'-TGAAATTATT-TATAATCTGGGTTTTGTGTCTT-3' and

S1.18cR (Seq. Id No. 10): 5'-CATCGGGAA-GAGCTAAGTTAAAAGTTGTG-3'.

To amplify exon 10 of the SREBP-2 gene including its exon/intron boundaries, the oligonucleotides EcoR I S2.10F (Seq. Id. No. 15): 5'-CGGAATTCGCCAGTGACCATTAA-CACCTTTTGA-3' and EcoR I S2.10R (Seq. Id. No. 16): 5'-CGGAATTCTG-CAGCAAGCCAGTCATCAGCAGCT-3' were used. PCR was performed in a final volume of 6 μl in 1× PCR buffer (Perkin Elmer) using 1.0 U Taq polymerase (Qiagen), 74 kBq [α-$^{32}$P]dCTP (Amersham) and final concentrations of 1.5 mM MgCl$_2$, 420 μM of each of the four dNTPs (Qiagen), and 8.3 μM of each of the two oligonucleotides.

For SSCP of the LDLR gene, genomic DNA (200 ng) was amplified under the following PCR conditions: 95° C., 180 sec. (1 cycle); 95° C., 45 sec.; 58° C., 30 sec., 72° C., 120 sec. (29 cycles).

For SSCP of the SREBP-1 and SREBP-2 genes, genomic DNA (200 ng) was amplified under the following PCR conditions: 95° C., 180 sec. (1 cycle); 95° C., 60 sec.; 58° C., 30 sec., 72° C., 60 sec. (30 cycles). Following PCR, 25 μl of denaturing buffer (95% formamide, 0.05% bromphenol blue, 0.05% xylencyanol, 20 mM EDTA) were added to the PCR mix. After 5 min. of denaturation at 95° C., 6 µl of the mix was loaded on a 7% polyacrylamide gel (acrylamide: bisacrylamide mix 37.5:1), 2×TBE, 1.37M glycerol, gel thickness 0.75 mm) and the gel was run with 1×TBE buffer at 4° C. in a cold room or at room temperature, at 15–20 V/cm for 12–16 h. Subsequently, the gel was dried under vacuum at 80° C. for 1 h and Kodak X-OMAT AR films were exposed for 3–36 h at room temperature.

b) Non-Radioactive Method

For non-radioactive detection of sequence variations in exon 10 of the SREBP-2 gene including its exon/intron boundaries, the oligonucleotides EcoR I S2.10F and EcoR I S2.10R were used. PCR was performed in a final volume of 11 µl in 1× PCR buffer (Qiagen) using 1.0 U Taq polymerase (Qiagen) and final concentrations of 1.5 mM $MgCl_2$, 909 µM of each of the four dNTPs (Qiagen), and 4.6 µM of each of the two oligonucleotides. Genomic DNA (100 ng) was amplified under the following conditions: 95° C., 180 sec. (1 cycle); 95° C., 60 sec.; 58° C., 30 sec.; 72° C., 60 sec. (29 cycles). Following PCR, 25 µl of denaturing or loading buffer, respectively, (97% formamide, 0.05% bromphenol blue, 0.05% xylencyanol, 10 mM NaOH) were added to the PCR mix. After 5 min. of denaturation at 92° C. and immediate chilling on ice for 10 min., 6 µl of the mix were loaded on Elchrom GMA Wide Mini S-50 gels, and run with 1× TAE buffer (9° C. buffer temperature) at 6 V/cm in an Elchrom Sea 2000 Submarine Electrophoresis Apparatus for 14 h. After removal of its backing, the gel was stained for 40 min. in 50 ml of SYBR® Gold (working solution according to the manufacturer, Molecular Probes) in 0.75×standard TAE buffer (4) on a shaker. Followed by destaining for 40 min. in 100 ml of distilled water by shaking, the gel was analyzed and digitalized using 302 nm UV transillumination on a Gel Doc 1000 system (BioRad).

4. Sequencing of Mutations in the LDLR Gene and of Mutations in SREBP-1, Exon 18c, and SREBP-2, Exon 10

The detected sequence variations were further analyzed by subcloning of the amplified exons and subsequent sequencing of the insert. In the LDLR gene, PCR amplification of the respective exons was performed using the oligonucleotides described above (3). In the SREBP-1 gene, PCR amplification of exon 18c was carried out using oligonucleotides containing additional Eco R I restriction sites;

Eco R I.S1.18cF (Seq. Id. No. 11): 5'-CGGAATTCT-GAAATTATTTATAATCTGGGTTTTGTGTC-3' and Eco R I S1.18cR (Seq. Id. No. 12): 5'-CGGAAT-TCATCGGGGAAGAGCTAAGTTAAAAGTTGTG-3'. In the SREBP-2 gene, PCR amplification of exon 10 was carried out using Eco R I.S2.10F: and Eco R I.S2.10R.

Amplification reactions were performed in a final volume of 50 µl in 1×PCR buffer (Qiagen) using 2.5 U Taq polymerase (Qiagen) and final concentrations of 1.5 mM $MgCl_2$, 500 µM of each of the dNTPs (Qiagen) and 2.0 µM of each of the two oligonucleotides. The following temperatures were reached on a RoboCycler®: 95° C., 45 sec.; 58° C., 30 sec.; 72° C., 45 sec. (30 cycles).

The amplified fragments (50 µl) were loaded on a 1% agarose gel containing 0.6 µg/ml ethidium bromide, cut out of the gel, and purified using the QIAquick™ Extraction kit (Qiagen). The DNA fragment was digested with 20 U EcoR I for at least 3 h and purified using the QIAquick® PCR purification kit. The vector pcDNA 3.1 His A (3–5 µg) was digested with 40 U EcoR I for 3 h. Subsequently, 20 U of calf intestinal peptide (Roche Diagnostics) were added and incubated for 1 h at 37° C. The vector was purified using the QIAquick™ PCR purification kit and eluated with 50 µl water. Ligation was performed using the ligation kit of Takara. The purified PCR product (4 µl) and the purified pcDNA3.1 His A vector (1 µl) were ligated according to the manufacturer and transformed into E. coli DH5α bacteria (Life Technologies) by using the heat shock method (42° C. for 45 sec.). From subjects with the wild type according to the SSCP results and from subjects with the sequence variation, 5–7 colonies were selected and resuspended in 10 µl of water. Genotypization for the presence of the sequence variation was performed using 2 µl of the bacterial suspension and the SSCP methods as described above. Independent clones of each of the two condition (wild type/mutation) from two independent PCR reactions were sequenced. DNA sequencing was performed by Microsynth Inc. using the dideoxy chain termination method. For expansion of the clones, 5 µl of the remaining suspension were added to 3 ml of LB medium containing 100 µg/ml ampicillin and incubated at 37° C. overnight. From 1.5 ml of the bacterial suspension, plasmid DNA was purified using the QIAprep™ Spin Miniprep kit (Qiagen).

5. Testing for Apolipoprotein E Mutations Known to Modify the Plasma Cholesterol Concentration The two frequent apo E aminoacid polymorphisms C112R and R158C were identified by PCR amplification and subsequent digestion with Hha I or its isoschizomer Cfo I according to the protocol of Hixson and Vernier (5).

6. Testing for Apolipoprotein B Mutations Known to Modify the Plasma Cholesterol Concentration Three different molecular assays were used to screen for mutations causing an amino acid substitution at position 3'500 of the apo B gene. Samples of subjects from the SPREAD study (2) with total cholesterol concentrations ≦4.5 mmol/L were pooled (25 samples) and screened for mutations using the methods of Ruzicka et al., 1992 (6) and of Schuster et al. (7). Subjects with total cholesterol concentrations >4.5 mmol/L and positive pools in the SPREAD study as well as all the other samples investigated until 1996 were tested individually using allele-specific, asymmetric PCR as described previously (2). Starting from 1996, this method was replaced by a site-directed mutagenesis PCR technique introducing an Msp I restriction site in the wild-type samples. Subsequent digestion with Msp I (8) revealed subjects affected by the R3'500Q mutation.

7. Methods to Identify the Polymorphisms in Exon 18c of SREBP-1 and Exon 10 of SREBP-2 by Restriction Enzyme Digestion In the SREBP-1 gene, the entire exon 18c containing the polymorphism which creates a variable Xmn I restriction site was amplified using the primer pair S1.18cF and S1.18cR.

In the SREBP-2 gene, only the 5' part of exon 10 containing the polymorphism which creates a variable Msp I restriction site was amplified. Thus, we could prevent that further Msp I sites were amplified and avoid a complex restriction pattern. In the SREBP-2 gene, the following oligonucleotides were used:

S2.10P.F (Seq. Id. No. 13) 5'-GCCAGTGACCATTAA-CACCTTTTGA -3' and

S2.10P.R (Seq. Id. No. 14) 5'-TCGTCTTCAAAGCCT-GCCTCAGTGGCTGGC-3'.

To detect the SREBP-1 polymorphism 80 ng genomic DNA from the individuals studied were amplified under the following PCR conditions: 95° C., 240 sec. (1 cycle); 95° C., 60 sec.; 55° C., 60 sec.; 72° C., 90 sec. (33 cycles). In a total volume of 25 µl, 2.0 µM of each of the two oligonucleotides, 400 µM of each of the dNTPs (Qiagen), 1× PCR buffer (1.5 mM $MgCl_2$ final concentration, Perkin Elmer), and 0.6 U Taq polymerase (Qiagen) were mixed. Of the unpurified amplicon, 20 μl were digested in 1× NE buffer using 16–32 U of Xmn I (New England Laboratories), 0.2 μl 10 mg/ml of BSA, and an incubation temperature of 37° C. for 5 h.

For the SREBP-2 polymorphism approximately 100 ng genomic DNA were PCR-amplified under the following conditions: 95° C., 30 sec.; 58° C., 30 sec.; 72° C., 90 sec. (30 cycles). In a total volume of 25 μl, 1.37 μM of each of the two oligonucleotides, 390 μM of each of the dNTPs (Qiagen), 1×PCR buffer (1.5 mM $MgCl_2$ final concentration, Perkin Elmer), and 0.75 U Taq polymerase (Qiagen) were mixed. Of the resulting amplicon, 20 μl were digested in 1× NE buffer using 16 U of Msp I and an incubation temperature of 37° C. for 5 h.

For the identification of the two polymorphisms, 6–8 μl of the digested reaction mixes were loaded on 10% polyacrylamide Ready Gels (BioRad) and run with 1× TBE buffer at room temperature at 18–22 V/cm for 25–35 min. The gels were subsequently stained in a 50 ml 0.5 μg/ml ethidium bromide solution for 5 min. and digitalized on a Gel Doc 1000 system from BioRad at 302 nm UV transillumination.

8. Testing for LDL Receptor Mutations as a Cause for Increased Plasma Cholesterol Concentrations In a subset of 48 individuals the clinical diagnosis of familial hypercholesterolemia caused by an LDLR defect was confirmed by cosegregation studies using ten different RFLPs in the LDLR gene (9,10). In 110 of a total of 446 kindreds, all exons of the LDLR gene were investigated using SSCP (radioactive method) and the published oligonucleotides (3). In 22 kindreds the presence of LDLR mutations was confirmed by subcloning and sequencing the exons containing the respective sequence variations.

9. Statistical Analysis: Population Genetics

Data from the Geneva Survey, a study in schoolchildren (13), and data from the Swiss MONICA study (including 3'341 individuals (14)), were used to assess age and gender-specific $90^{th}$ percentiles for total cholesterol and triglycerides in Switzerland. All calculations were performed on Macintosh G3 computers using the File-Maker® Database CARDIOFILE, the StatView® and SuperANOVA® programs.

Subjects having plasma cholesterol concentrations below the $90^{th}$ percentile were classified as normocholesterolemic (NC), subjects having total cholesterol concentrations above the $90^{th}$ percentile were classified as hypercholesterolemic (HC). For both groups, the influence of the presence of the Apo E C112R and R158C mutations, and the novel amino acid polymorphisms in the SREBP-2 gene (A595G) and in the SREBP-1 gene (G1028G) were assessed using multivariate analysis.

10. Evaluation of the Results Obtained According to the Above Mentioned Indications 10.1. Association of Polymorphisms in the SREBP-1 and -2 Genes with Plasma Cholesterol Levels 10.1.1. Detection of Mutations in the SREBP-1 and -2 Genes with PIC-Values Above 0.25

A sample of subjects was investigated for the presence of sequence variations using the single-strand-conformation polymorphism method (SSCP). Our aim was to detect polymorphisms whose prevalence was high enough to allow analyses by population genetics methods. For that purpose we defined a Polymorphism Information Content (PIC)—value above 0.25. Two sequence variations, one in exon 18c of the SREBP-1 gene and one in exon 10 of the SREBP-2 gene, detected by SSCP, fulfilled this requirement and were further characterized. Exon 18c of the SREBP-1 gene and exon 10 of the SREBP-2 gene were amplified in subjects having the respective SSCP patterns differing from the wild-type. These exon sequences were subcloned and sequenced.

FIG. 1A shows the chromatogram of a subject having a DNA polymorphism at the amino acid position 1028 in exon 18c of the SREBP-1 gene (G1028G). FIG. 1B shows the chromatogram of a subject having a DNA polymorphism causing an amino acid substitution at position 595 of the SREBP-2 (A595G).

In the SREBP-1 gene, a base substitution C→G in exon 18c was discovered. This base substitution does not lead to an amino acid exchange, but generates an Xmn I restriction site (FIG. 1A). In the SREBP-2 gene, a base substitution C→G was detected. This base substitution leads to an exchange of alanine by glycine in the amino acid sequence and generates an additional Msp I restriction site (FIG. 1).

The corresponding PIC—values, calculated from all the subjects enrolled except the related individuals from the SIBSHIP study (N=2'446), were 0.368 for the SREBP-1 gene polymorphism and 0.300 for the SREBP-2 gene polymorphism. In order to screen larger population samples for these polymorphisms, we developed a method for each of the two polymorphisms consisting in a PCR amplification of the corresponding DNA fragment and subsequent restriction enzyme digestion (FIG. 2). Neither the G1028G polymorphism nor the A595G polymorphism did significantly differ from the Hardy-Weinberg equilibrium (P>0.70, P>0.10, respectively, if a recessive effect was assumed).

In HeLa cells the G1028G polymorpism was detected in only one of the two alleles (heterozygous for the G1028G polymorphism (12)). The A595G mutation was absent in HeLa cells (homozygous for the A595A polymorphism (11)).

10.1.2. Population Genetics

A total of 3'078 individuals were enrolled. Two thousand six hundred individuals whose pretreatment total cholesterol levels had been measured were genotyped for the mutations and polymorphisms in four genes. A subgroup of 954 individuals were from randomly collected samples of cross-sectional surveys (SPREAD, IDA), 318 were unrelated individuals from the SIBSHIP study (one unaffected individual per family and all spouses, brothers and sisters in law who were genetically unrelated (REL). A total of 871 individuals were enrolled from groups of patients with primary and secondary hyperlipoproteinemias. All 3'078 individuals of the groups of patients and the controls were screened for the presence of the mutation in the apo B-100 gene leading to an amino acid exchange at position 3'500 in order to identify patients with FDB in control samples and samples of patients with hyperlipoproteinemias. To identify patients with familial dysbetalipoproteinemia, all 3'078 individuals were also screened for the presence of the mutation in the apo E gene at amino acid position 158 (E2 allele) as well as for the presence for the mutation at position 112 (E4 allele). The presence of LDLR gene defects leads as a rule to a significant, i.e. two- or threefold increase of total cholesterol concentrations, therefore only patients suffering from primary forms of hyperlipoproteinemias and clearly increased total cholesterol concentrations were tested for the presence of these mutations. Table 1 presents a summary of the different samples of patients and controls. Individuals identified in the control samples as having specific disorders leading to primary or secondary forms of hyperlipoproteinemia, respectively, were also included in the groups of patients having the respective disorder. Thus, the sum of subjects from all subgroups exceeds the total number of subjects (N=2'600). Table 1 stratifies the groups of patients and controls according to individuals with total cholesterol concentrations below the 90th percentile (normocholesterolemic, NC) and individuals with total cholesterol concentrations above the 90th percentile (hypercholesterolemic, HC).

The groups of patients and the controls listed in Table 1 were screened for the presence of the polymorphism described by using the methods indicated above (large scale, high throughput screening).

Three further genes were investigated: the apo E gene (amino acid polymorphisms C112R and R158C), the apo B-100 gene (mutation at amino acid position 3'500, R3'500Q). In the LDL receptor gene, mutations causing familial hypercholesterolemia were identified by using SSCP, subsequent amplification of the respective exons in which sequence variations were detected, subcloning, and sequencing.

A total of 3'078 subjects were investigated for the presence of the amino acid substitution in the apo B gene (R3'500Q), and for the presence of two amino acid polymorphisms in the apo E gene (C112R or E4 allele, R158C or E2 allele). All three mutations are known to modify the plasma cholesterol concentration.

In addition, 2'600 subjects were investigated for the novel DNA polymorphism in the SREBP-1 gene (G1028G) which was used as a marker. All 3'078 subjects were investigated for the novel DNA polymorphism in the SREBP-2 gene (A595G) causing an amino acid substitution.

In these subjects, plasma total cholesterol concentrations were measured. From the 3'078 subjects enrolled, 478 subjects took lipid-lowering drugs at study entry and pretreatment total cholesterol concentrations were not available. Therefore, these subjects were excluded from further analyses. Of the remaining 2'600 subjects pretreatment plasma total cholesterol concentrations adjusted for an age of 50 years as described were then included for further analysis. Table 2 summarizes the results of the prevalence of the two polymorphisms in the respective subgroups of patients and controls as well as the mean total cholesterol concentrations of the different subgroups in relation to the presence of the polymorphism.

Overall, a highly significant, cholesterol-lowering effect of the A595G mutation in the SREBP-2 gene was observed (Table 2, N=2'600; P=0.0005). This effect was even more pronounced, when subjects homozygous for the C112R mutation in the apo E gene (E4/E4) (N=107) were excluded from analysis (N=2'493; P<0.0001). If only genetically unrelated subjects were used in the analysis, thus excluding relatives from the SIBSHIP study, the probability for the difference being by chance decreased even more (N=2'446, P=0.0003). FIG. 3 shows the analysis of the sample of unrelated subjects (N=2'446) which consisted of all subjects except the genetically related subjects from the SIBSHIP study, after stratification using different criteria. FIGS. 3A and B show the effect of the G1028G and the A595G polymorphisms in randomly selected subjects. Random samples (designated as such) with respect to hypercholesterolemia were the SPREAD and IDA studies as well as the samples of unrelated, unaffected individuals (REL), and subjects collected because of a possible impairment of their memory functions (MCS). The other samples were selected because of the presence of hypercholesterolemia (non-random). Using analyses of variance (ANOVA,Scheffé's test), a significant effect was detected for the G1028G polymorphism, when the sample was stratified according to the selection groups (random/non-random) (P=0.0164). Likewise, the effect was detected in both groups with regard to the A595G mutation; ANOVA resulted in a probability for the difference being due to chance of P<0.0001. FIGS. 3C and D present the stratification with respect to the $90^{th}$ percentile (NC, HC). In the G1028G polymorphism there was a significant effect when ANOVA was used (P=0.0088). In the A595G mutation analysis after inclusion of the additional factor resulted in a probability of P<0.0001 as well.

In addition, the known cholesterol-modifying effect of the apo E gene polymorphisms C112R ($\epsilon$4) and R158C ($\epsilon$2) could be demonstrated in our study population (N=2'600; P<0.0001).

FIGS. 3E and F demonstrate the gene—gene interactions between apo E and the SREBP-1 and -2 genes. No significant, cholesterol-modifying effect of the G1028G polymorphism in the SREBP-1 gene was detected when all 2'600 subjects were included in the analysis. After inclusion of the effects of the apo E genes into the analysis, in the G1028G polymorphism, the difference between the homozygous form of the polymorphism (22) and the two other alleles (11/12) was not significant (ANOVA, P=0.0722). However, when subjects homozygous or heterozygous for the apo E C112R (E4) mutation were excluded (N=761), the effect of the absence of the wild-type allele on plasma total cholesterol levels was highly significant (N=1'839; P<0.0001). In the A595G polymorphism the difference between the homozygous form of the wildtype (11) and the two other alleles (12/22) was already highly significant (P=0.0002) after inclusion of the effects of the apo E gene in the analysis. When subjects homozygous or heterozygous for the apo E C112R (E4) mutation were excluded, the probability of the effect being due to chance decreased even further (P<0.0001).

Further stratification of the samples according to the underlying disorders either as a cause of a primary or of a secondary hypercholesterolemia is summarized in Table 2. The results of the prevalence calculations of the two polymorphisms (G1028G, A595G) according to the different subgroups are shown in the first line. The results of the pretreatment total cholesterol mean values in the different subgroups, stratified for the presence or absence of the G1028G and A595G polymorphisms, are shown in the second line (Table 2). Regarding the subgroups with primary hyperlipidemias, the effect of the A595G mutation achieved statistical significance in the group of patients with FDL (P=0.0020) and in the group of patients with primary hypercholesterolemia (PHC). In these patients mutations in the apo E, apo B, and LDLR genes had been excluded, although an autosomal dominantly or recessively inherited gene defect was suspected as a cause for hypercholesterolemia. In this latter sample, the prevalence of the wild-type (11) allele was significantly higher (9.38%) than in the sum of the other samples (6.69%) (P=0.0328).

Regarding the samples of subjects with secondary hyperlipoproteinemias (which included both NC and HC subjects), in male subjects with diabetes mellitus and normal plasma triglyceride concentrations (TG<2.3 mmol/L) there was a significant difference between A595A (11) and A595G (12/22) positive individuals (P=0.0018). In 11.6% of the subjects with secondary hyperlipoproteinemias plasma triglyceride concentrations were increased.

In the SREBP-1 gene, the prevalence of the wild-type allele in its homozygous state (11) was 40.35%, the prevalence of the G1028G polymorphism was in its heterozygous state (12) 45.62% and in its homozygous state (22) 14.04% (N=2'600). In the SREBP-2 gene, the prevalence of the wild-type in its homozygous state (11) was 6.69%, the prevalence of the A595G mutation was in its heterozygous state (12) was 35.15% and in its homozygous state (22) 58.15% (N=2'600).

To elucidate the effect of the discovered DNA and amino acid polymorphisms on plasma total cholesterol levels, 3'078 individuals were tested molecularly. In 2'600 subjects, demographic as well as clinical data could be completed with age, gender, total cholesterol concentrations without treatment with lipid-lowering drugs at the time of cholesterol determination, genotypes with respect to the apo E amino acid polymorphisms (C112R or ε4 allele, R158C or ε2 allele), and the apo B100 mutation first discovered to be responsible for FDB (R3'500Q). The R158C amino acid polymorphism had, in its homozygous state, a cholesterol-modifying effect in the population studied (P<0.0001). In subjects positive for the R3'500Q mutation (FDB), total cholesterol concentrations were increased compared to the apo B defect negative individuals (P<0.0001). In subjects with confirmed LDL receptor mutations (FHM), mean total cholesterol concentrations were increased compared to controls (P<0.0001). Overall, the DNA polymorphism detected in the SREBP-1 gene (G1028G) did not significantly modify plasma total cholesterol concentrations in these subjects. However, in combination with the presence of the apo B R3'500Q mutation, the G1028G (22) polymorphism was significantly associated with an increase in plasma cholesterol concentrations (P=0.0097). Further stratification of the subjects involved in the study according to the underlying genetic disorders or according to the clinical diagnosis confirmed the effect of the novel SREBP-2 amino acid polymorphism on plasma total cholesterol concentrations in almost all groups, but none of the differences achieved statistical significance except in the group of patients with familial dysbetalipoproteinemia, FDL, and in subjects having hypercholesterolemia due to unknown gene defects (PHC).

10.2 Association of the Novel A595G Mutation with Senile Dementia of the Alzheimer Type Another remarkable result of the present study was the significant prevalence of the wild type allele (A595A) compared to the amino acid substitution (A595G) when a sample of clinically diagnosed Alzheimer's patients was compared with the prevalence in the general population (Table 2, 2.4% versus 7.0%, P=0.0234).

Figure 4:
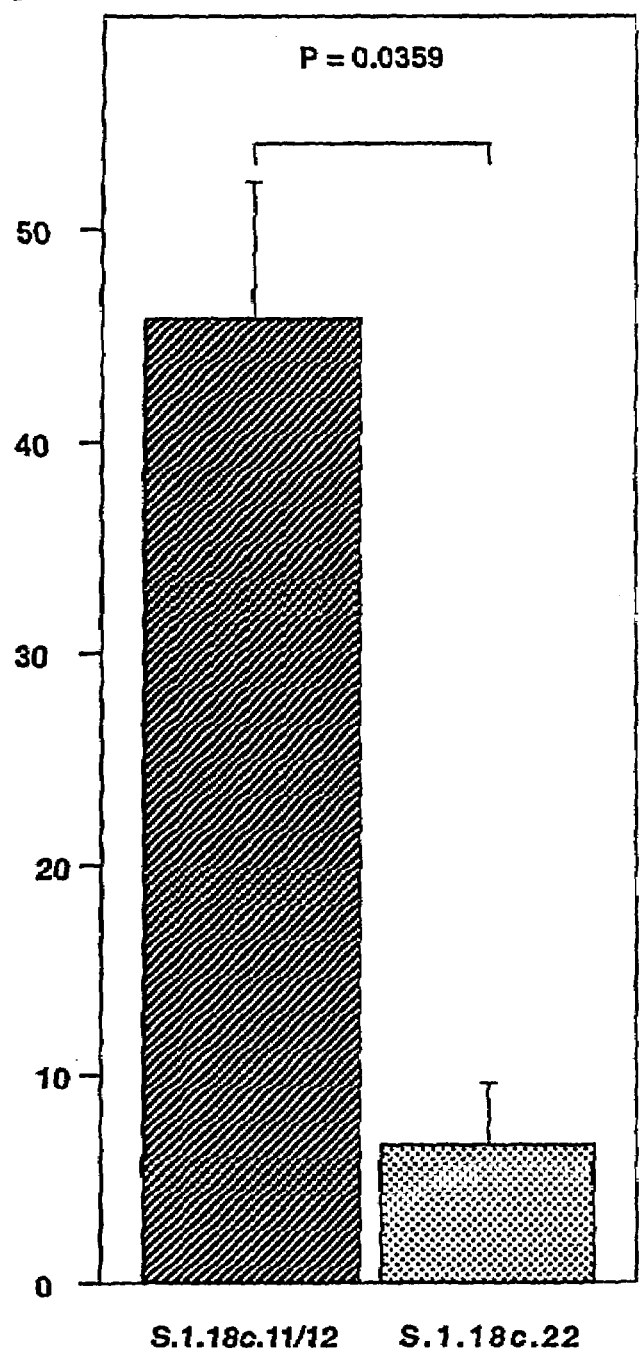
FIG. 4 shows the percentage alteration of the plasma cholesterol levels before and after administration of protease inhibitors depending on G1028G polymorphism.

10.3. Association of the Novel G1028G Polymorphism with the Absence of an Increase of the Plasma Lipid Concentration Following Administration of Protease-Inhibitors in HIV Patients The results concerning differences in the prevalence are also shown in Table 2 (P=0.0339). FIG. 4 presents the percent change of the plasma cholesterol concentration before and after administration of protease-inhibitors, depending on the G1028G polymorphism.

11. Study Comprising Polymorphism in Exon 6 of SREBP-2

11.1. Basics

Probands

A total of 1081 probands from the same groups as mentioned above (711 from the SPREAD study, 346 from the IDA study as well as 24 from a prospectively examined collective of people who died in Basel (PATH study)) were enrolled in this study.

Material

In addition to the already described materials, restriction enzyme Dde I (New England Biolabs) was used.

Methods

Subjects enrolled in the study were additionally tested for a further mutation in the SREBP-2 gene (exon 6) leading to an amino acid substitution (R371K).

The SREBP-2 R371K mutation was essentially investigated as already described. In particular, the lipoprotein analysis, the DNA extraction method as well as the determination of the single stranded confirmation polymorphism by means of the non-radioactive method were performed as described above.

11.2 Sequencing of the Exon 6 Mutation of SREBP-2

Sequencing was performed as described previously with the following modifications: exon 6 in the SREBP-2 gene was amplified by means of the oligonucleotides EcoRI.S2.6F (Seq. Id. No. 17): 5' CGGAATTCTGGTCT-CACT GTGTTTTCACTCATC 3' and EcoR I.S2.6R (Seq. Id. No. 18): 5'-CG-GAATTCGCCAGGGCTGACAAGC-CTTTTCTCA-3'. Amplification reaction was performed in a total volume of 50 µl in 1× PCR buffer (Qiagen) using 0.4 U Taq polymerase (Qiagen) and final concentrations of 3.5 mM $MgCl_2$, 455 µM of each of the four dNTP (Qiagen) and 2.0 µM of each of the two oligonucleotides at the following temperatures: 94° C., 45 sec.; 56° C., 30 sec; 72° C., 60 sec. (32 cycles). The amplified fragments were analyzed by means of subcloning and subsequent sequencing of the insert (as already described).

11.3 Methods for the Identification of SREBP-2, Exon 6 Mutation by Restriction Enzyme Digest To detect the SREBP-2 mutation (exon 6, R371K) about 100 ng genomic DNA was amplified by the already described methods using oligonucleotides EcoR I.S2.6F and EcoR I.S2.6R. 20 µl were digested with 7 U Dde I in 1× NE buffer at a incubation temperature of 37° C. for 5 hours. 4 µl 5× non denaturing loading buffer (E1-chrom) were added to the reaction mixture. 7 µl of said mixture were loaded on Spreadex Wide-Mini S-100 gels (E1-chrom), run at 55° C. at 10V/cm for 25–45 minutes, destained with distilled water (40 minutes) and digitalized on a Gel Doc 1000 system.

11.4 Statistical Methods

To compare the prevalences of sequence variations in the SREBP-1 and SREBP-2 genes the Chi-square test was used.

11.5 Evaluation of the Results Obtained According to the Above Indications

The 698 probands of the SPREAD study had an age median of 20.5 years (age range 18.8–43.7), the 370 probands of the IDA study had an age median of 74.5 years (age range 47.0–95.4 years). The comparison of the two groups of probands who were not selected but had a different age, showed statistically significant differences concerning the presence of SREBP-1 and SREBP-2 mutations.

The prevalence of the absence of SREPB-1c-G1028G polymorphism in homozygous form (i.e. genotype 11/12) in subjects of the SPREAD study was 622/711 (87.5%) compared to 304/367 (82%) in the subjects of the IDA/PATH study. This makes an absolute difference of −4.7% (relative −5.4%, respectively) with a P-value of 0.038 (Chi square test).

The prevalence of the absence of the SREBP-2 A595G polymorphism in homozygous form (i.e. genotype 11/12) in probands of the SPREAD study was 305/711 (43%) compared to 135/370 (36.5%) in probands of the IDA/PATH study. This makes an absolute difference of −6.8% (relative −15.1%, respectively) with a P-value of 0.041.

The prevalence of the SREBP-2 R371K mutation in probands of the SPRED study was 19/698 (2.7%) compared to 3/370 (0.8%) in probands of the IDA/PATH study. This makes an absolute difference of −1.9% (relative −70.4%, respectively) with a P-value of 0.036.

11.6 Discussion

The differences in the prevalence data in the groups of younger or older probands, respectively, can only be explained by mortality differences since both random samples were taken from the same population.

Thus, in the IDA/PATH study population with an age median of 74.5 years numerous probands who are carriers of the SREPB-2 G1028G genotype 11/12 have already died: 316 carriers were expected in this group based on the data of the SPREAD study but only 304 probands were observed with this genotype (11/12), this means that 12 probands are missing in this group.

The same is true for carriers of the SREBP-2 A595G genotype 11/12: 159 carriers were expected in this group based on the data of the SPREAD study but only 135 probands with this genotype (11/12) were observed, 24 probands are therefore missing in this group.

The same is true for the rare carriers of the SREBP-2 R371K mutation: 10 carriers were expected based on the data of the SPREAD study but only 3 probands with this mutation were observed, 7 probands are therefore missing in this group.

One explanation for the significantly lower prevalence of certain sequence variations in SREBP-1 and SREBP-2 is the higher mortality of carriers of the genotypes SREBP-1.18c (11/12), SREBP-2.10 (11/12) and of the carriers of the SREBP-2 R371K mutation. This can for example be due to the already described association for the elevation of the plasma cholesterol level resulting in a coronary heart disease but as well due to the disproportionate occurrence of diseases such as e.g. senile dementia of the Alzheimer's type as already described, the two mentioned risk factors or combinations with further risk factors.

TABLE 1

| Sample | Studies | Sample characterization | Age Mean | Gender m/(m + w) | All subjects A | All subjects TC Mean (± ISD) | Normo-cholesterolemic-subjects[1] A | Normo-cholesterolemic-subjects[1] TC Mean (± ISD) | Hyper-cholesterolemic subjects[1] A | Hyper-cholesterolemic subjects[1] TC Mean (± ISD) |
|---|---|---|---|---|---|---|---|---|---|---|
| All subjects | | | | | | | | | | |
| TTL | SPREAD, SIBSHIP IDA, MCS, STARTER | All ages | 45.55 | 0.66 | 2'600 | 6.84 ± 2.52 | 1'980 | 5.80 ± 1.32 | 620 | 10.14 ± 2.58 |
| Samples of subjects who were randomly selected | | | | | | | | | | |
| RDM.YNG | SPREAD | Random sample (young) | 20.77 | 1.00 | 630 | 5.12 ± 0.88 | 612 | 5.05 ± 0.78 | 18 | 7.40 ± 1.17 |
| RDM.ELD | IDA | Random sample (elderly) | 75.98 | 0.67 | 324 | 6.46 ± 1.49 | 316 | 6.39 ± 1.45 | 8 | 8.93 ± 1.01 |
| Samples of subjects with disorders causing primary hyperliproproteinemias | | | | | | | | | | |
| FDL | SPREAD, SIBSHIP IDA, MCS, STARTER | Apolipoprotein E defect (R158C, homozygous) | 46.17 | 0.76 | 46 | 9.90 ± 4.10 | 15 | 5.27 ± 1.43 | 31 | 12.15 ± 2.89 → FDL |
| FDB | SPREAD, SIBSHIP IDA, MCS, STARTER | Apolipoprotein B defect (R3'500Q, heterozygous) | 41.49 | 0.54 | 37 | 9.046 ± 1.341 | 5 | 6.93 ± 0.86 | 32 | 9.38 ± 1.08 → FDB |
| FHM | SIBSHIP | LDLR defect (molekular-genet. detected) | 34.87 | 0.51 | 74 | 10.93 ± 2.43 | | | 74 | 10.93 ± 2.43 → FH |
| PHC | SIBSHIP | Primary, isolated hyper-cholesterolemia[2] | 40.58 | 0.55 | 341 | 9.90 ± 2.62 | — | — | 341 | 9.90 ± 2.62 |
| PCH | SIBSHIP | Primary, combined hyper-lipoproteinemia[2] | 47.48 | 0.82 | 85 | 9.98 ± 2.22 | — | — | 85 | 9.98 ± 2.22 → FCH |
| REL | SIBSHIP | Relatives, not affected[3] | 40.19 | 0.54 | 318 | 6.39 ± 1.19 | 310 | 635 ± 1.17 | 8 | 8.11 ± 0.34 |
| Samples of subjects with disorders causing secondary hyperliproproteinemias[4] | | | | | | | | | | |
| DIA | STARTER, SIBSHIP IDA, MCS | Diabetes mellitus (Glucose Plasma >7.8 mmol/L) | 50.96 | 0.59 | 229 | 6.48 ± 1.97 | 191 | 5.87 ± 1.21 | 38 | 9.55 ± 2.20 SHL |
| RIN | STARTER, SIBSHIP IDA, MCS | Renal insufficiency (Clearing cr <50 ml/min.)) | 76.63 | 0.44 | 131 | 7.17 ± 2.68 | 115 | 6.83 ± 2.58 | 16 | 9.65 ± 2.07 SHL |
| LIV | STARTER, SIBSHIP IDA, MCS | Alcohol consumption >60 g/T and/or γ-GT >664/l | 53.32 | 0.85 | 151 | 8.22 ± 2.89 | 86 | 6.49 ± 1.25 | 65 | 10.52 ± 2.84 SHL |
| HTH | STARTER, SIBSHIP IDA, MCS | Hypothyroidism (TSH >4.0 mIU/L) | 59.53 | 0.15 | 102 | 6.54 ± 1.97 | 86 | 5.92 ± 1.02 | 16 | 9.86 ± 2.49 SHL |
| Samples of subjects with potentially SREBP-1 and/or-2-related disorders | | | | | | | | | | |
| MEM.TTL | MCS | Adults (all age groups) | 70.63 | 0.46 | 413 | 6.24 ± 1.67 | 387 | 6.09 ± 1.61 | 26 | 8.39 ± 0.93 |

TABLE 1-continued

| Sample | Studies | Sample characterization | Age Mean | Gender m/(m + w) | All subjects A | All subjects TC Mean (± ISD) | Normo-cholesterolemic-subjects[1] A | Normo-cholesterolemic-subjects[1] TC Mean (± ISD) | Hyper-cholesterolemic subjects[1] A | Hyper-cholesterolemic subjects[1] TC Mean (± ISD) |
|---|---|---|---|---|---|---|---|---|---|---|
| MEM.DAT | | Dementia of Alzheimer Type (MMS <26) | 73.50 | 41.2 | 165 | 6.16 ± 1.31 | 157 | 6.06 ± 1.25 | 8 | 8.17 ± 0.61 |
| HIV.STB | STARTER | TC, not increasing with protease inhibitors[5] | 34.24 | 80.0 | 25 | 4.79 ± 1.31 | 24 | 4.70 ± 1.25 | 1 | 7.05 |
| HIV.INC | | TC, increasing with Protease inhibitors[5] | 38.06 | 85.0 | 20 | 4.52 ± 0.91 | 20 | 4.52 ± 0.91 | | |

[1] Normocholesterolemic: Plasma cholesterol <90th percentile, age and sex-matched; hypercholesterolemic: Plasma cholesterol >90th percentile, age and sex-matched
[2] Underlying molecular defects not known
[3] Only unrelated individuals (one non-affected person per family and all spouses, brothers in law and sisters in law genetically unrelated)
[4] Combined samples from individuals collected because of secondary hyperlipoproteinemias plus subjects collected from the other samples
[5] HIV positive individuals who experience no increase (STB) or an increase in total cholesterol plasma concentrations following administration of protease inhibitors (INC)

TABLE 2

| Sample | Prevalence[1] TC Mean[2] | SREBP-1 Polymorphism (G1028G) 11 | 12 | 22 | P ΔTC[5] | P ΔPR[3] |
|---|---|---|---|---|---|---|
| All Subjects | | | | | | |
| TTL | PR | 40.35 (1'049) | 45.62 (1'186) | 14.04 (365) | | |
| | TC | 6.74 ± 2.47 | 6.88 ± 2.53 | 6.99 ± 2.61 | 0.2309 | |
| Samples of subject who were randomly selected | | | | | | |
| RDM.YNG | PR | 41.75 (263) | 45.71 (288) | 12.54 (79) | | 0.3270 |
| | TC | 5.04 ± 0.87 | 5.15 ± 0.90 | 5.24 ± 0.87 | 0.1735 | |
| RDM.ELD | PR | 41.36 (134) | 40.74 (132) | 17.90 (58) | | 0.0324 |
| | TC | 6.50 ± 1.55 | 6.41 ± 1.41 | 6.36 ± 1.53 | 0.5796 | |
| Samples of subjects with disorders causing primary hyperliproproteinemias | | | | | | |
| FDL | PR | 32.26 (10) | 41.94 (13) | 25.81 (8) | | 0.0578 |
| | TC | 12.63 ± 2.78 | 11.54 ± 3.37 | 12.96 ± 2.15 | 0.4351 | |
| FDB | PR | 33.33 (12) | 38.89 (14) | 16.67 (6) | | 0.4401 |
| | TC | 9.99 ± 0.98 | 9.06 ± 1.12 | 8.92 ± 0.68 | 0.2393 | |
| FHM | PR | 33.78 (75) | 48.65 (36) | 17.57 (13) | | 0.3753 |
| | TC | 11.55 ± 1.98 | 10.56 ± 2.09 | 10.74 ± 3.58 | 0.7579 | |
| PHC | PR | 38.12 (130) | 48.09 (164) | 13.78 (47) | | 0.8842 |
| | TC | 9.74 ± 2.31 | 10.04 ± 2.97 | 9.85 ± 2.06 | 0.8737 | |
| PCH | PR | 41.18 (35) | 43.53 (37) | 15.29 (13) | | 0.7347 |
| | TC | 9.97 ± 2.46 | 9.81 ± 1.82 | 10.50 ± 2.69 | 0.3650 | |
| REL | PR | 39.62 (126) | 46.86 (149) | 13.52 (43) | | 0.7772 |
| | TC | 6.38 ± 1.16 | 6.44 ± 1.09 | 6.27 ± 1.55 | 0.4679 | |
| Samples of subjects with disorders causing secondary hyperliproproteinemias[4] | | | | | | |
| DIA | PR | 39.30 (90) | 43.67 (100) | 17.03 (39) | | 0.1723 |
| | TC | 6.47 ± 1.78 | 6.44 ± 1.88 | 6.62 ± 2.57 | 0.6233 | |
| RIN | PR | 40.46 (53) | 45.80 (60) | 13.74 (18) | | 0.9197 |
| | TC | 7.27 ± 3.37 | 7.15 ± 2.01 | 6.96 ± 2.49 | 0.7193 | |
| LIV | PR | 38.51 (57) | 47.30 (70) | 14.19 (21) | | 0.9567 |
| | TC | 8.14 ± 2.55 | 8.53 ± 3.31 | 7.92 ± 2.11 | 0.6011 | |
| HTH | PR | 37.63 (35) | 46.24 (43) | 16.13 (15) | | 0.5545 |
| | TC | 6.17 ± 1.80 | 6.55 ± 1.87 | 6.00 ± 1.29 | 0.2678 | |
| Samples of subjects with potentially SREBP-1 and/or-2-related disorders | | | | | | |
| TTL - DAT | PR | 40.16 (978) | 45.59 (1'110) | 14.25 (347) | | |
| | TC | 6.78 ± 2.53 | 6.82 ± 2.58 | 7.05 ± 2.63 | 0.2225 | |
| DAT | PR | 43.03 (71) | 46.06 (76) | 10.91 (18) | | 0.2318 |
| | TC | 6.14 ± 1.22 | 6.24 ± 1.28 | 5.92 ± 1.78 | 0.4050 | |
| HIV.STB | PR | 52.00 (13) | 28.00 (7) | 20.00 (5) | | |
| | TC | 4.85 ± 1.53 | 4.27 ± 0.59 | 5.37 ± 1.37 | 0.2772 | |
| HIV.INC | PR | 40.00 (8) | 60.00 (12) | 0.00 (0) | | 0.0339 |
| | TC | 4.26 ± 1.03 | 4.70 ± 0.82 | — — | — | |

TABLE 2-continued

| | | SREBP-2 Polymorphism (A595G) | | | | |
|---|---|---|---|---|---|---|
| Sample | Prevalence[1] TC Mean[2] | 11 | 12 | 22 | P ΔTC[6] | P ΔPR[4] |
| All Subjects | | | | | | |
| TTL | PR | 6.69 (174) | 35.15 (914) | 58.15 (1'512) | | |
| | TC | 7.47 ± 3.48 | 6.83 ± 2.57 | 6.77 ± 2.34 | 0.0005 | |
| Samples of subject who were randomly selected | | | | | | |
| RDM.YNG | PR | 5.87 (37) | 36.51 (230) | 57.62 (363) | | 0.3445 |
| | TC | 5.15 ± 0.85 | 5.06 ± 0.91 | 5.15 ± 0.87 | 0.7943 | |
| RDM.ELD | PR | 5.56 (18) | 30.25 (98) | 64.20 (208) | | 0.3815 |
| | TC | 6.77 ± 1.51 | 6.55 ± 1.66 | 6.39 ± 1.40 | 0.3525 | |
| Samples of subjects with disorders causing primary hyperliproteinemias | | | | | | |
| FDL | PR | 9.68 (3) | 16.13 (5) | 74.19 (23) | | 0.5034 |
| | TC | 16.89 ± 3.45 | 10.62 ± 1.76 | 12.01 ± 2.47 | 0.0020 | |
| FDB | PR | 8.33 (3) | 44.44 (16) | 36.11 (13) | | 0.5412 |
| | TC | 8.63 ± 0.0.22 | 9.21 ± 1.09 | 9.77 ± 1.01 | 0.1989 | |
| FHM | PR | 8.11 (6) | 35.14 (26) | 56.76 (42) | | |
| | TC | 11.15 ± 2.34 | 11.06 ± 2.13 | 10.81 ± 2.59 | 0.8118 | |
| PHC | PR | 9.38 (32) | 37.24 ± (127) | 53.37 (182) | | 0.0328 |
| | TC | 10.89 ± 4.82 | 9.90 ± 2.20 | 9.72 ± 2.31 | 0.0240 | |
| PCH | PR | 10.59 (9) | 36.47 (31) | 52.94 (45) | | 0.1439 |
| | TC | 9.71 ± 2.23 | 10.35 ± 2.98 | 9.78 ± 1.53 | 0.7019 | |
| REL | PR | 6.60 (21) | 33.33 (106) | 60.06 (191) | | 0.9462 |
| | TC | 6.43 ± 1.10 | 6.33 ± 1.26 | 6.42 ± 1.16 | 0.8984 | |
| Samples of subjects with disorders causing secondary hyperliproteinemias[4] | | | | | | |
| DIA | PR | 6.55 (15) | 38.86 (89) | 54.59 (125) | | 0.9282 |
| | TC | 6.48 ± 1.69 | 6.47 ± 1.92 | 6.49 ± 2.05 | 0.9985 | |
| RIN | PR | 6.11 (8) | 40.46 (53) | 53.44 (70) | | |
| | TC | 7.44 ± 2.04 | 7.14 ± 3.42 | 7.16 ± 2.07 | 0.7692 | |
| LIV | PR | 8.11 (12) | 32.43 (48) | 61.49 (91) | | 0.5249 |
| | TC | 9.81 ± 4.78 | 8.02 ± 3.06 | 8.25 ± 2.43 | 0.0696 | |
| HTH | PR | 6.45 (6) | 24.73 (23) | 68.82 (64) | | 0.9246 |
| | TC | 7.46 ± 1.56 | 7.09 ± 2.78 | 6.00 ± 1.11 | 0.1174 | |
| Samples of subjects with potentially SREBP-1 and/or-2-related disorders | | | | | | |
| TTL - DAT | PR | 6.98 (170) | 34.99 (852) | 58.03 (1'413) | | |
| | TC | 7.48 ± 3.52 | 6.88 ± 2.63 | 6.81 ± 2.39 | 0.0018 | |
| DAT | PR | 2.42 (4) | 37.58 (62) | 60.00 (99) | | 0.0234 |
| | TC | 7.44 ± 1.19 | 6.14 ± 1.34 | 6.12 ± 1.28 | 0.0487 | |
| HIV.STB | PR | 16.00 (4) | 36.00 (9) | 48.00 (12) | | |
| | TC | 3.99 ± 0.62 | 4.77 ± 1.47 | 5.08 ± 1.32 | 0.1855 | |
| HIV.INC | PR | 5.00 (1) | 45.00 (9) | 50.00 (10) | | 0.2433 |
| | TC | 2.13 — | 4.80 ± 0.26 | 4.51 ± 0.98 | 0.0036 | |

[1] Prevalence (= PR) in percent (number of subject)
[2] Mean of plasma total cholesterol concentration (= TC) in mmol/L, (± SD)
[3] ΔPR = PR11/12 vs. PR22; significance level (P) of the difference between prevalence of sample (PR.Sample) vs. prevalence of all subjects (PR.TTL) minus prevalence of respective sample (PR.Sample): (P of PR.Sample vs. (PR.TTL-PR.Sample))
4 ΔPR = PR11 vs. PR12/22; significance level (P) of the difference between prevalence of sample (PR.Sample) vs. prevalence of subjects (PR.TTL) minus prevalence of respective sample (PR.Sample): (P of PR.Sample vs. (PR.TTL-PR.Sample))
[5] ΔTC = TC11/12 vs. TC22/
[6] ΔTC = TC11 vs. TC12/22

REFERENCES (Literature is directly cited in the text or the text refers to the below listed documents by quoting the corresponding quotation number (in brackets):

1. Miller, S. A. 1988. A simple salting out procedure for extracting DNA from human nucleated cells. *Nucleic Acids Res.* 16:1215.
2. Miserez, A. R., R. Laager, N. Chiodetti, and U. Keller. 1994. High prevalence of familial defective apolipoprotein B-100 in Switzerland. *J. Lipid Res.* 35:574–583.
3. Hobbs, H. H., M. S. Brown, and J. L. Goldstein. 1992. Molecular genetics of the LDL receptor gene in familial hypercholesterolemia. *Hum. Mutat.* 1:445–466.
4. Sambrook, J., E. F. Fritsch, and T. Maniatis. 1989. Molecular Cloning. A Laboratory Manual. *Cold Spring Harbor Laboratory Press*. Second Edition.
5. Hixson, J. E. and D. T. Vernier. 1990. Restriction isotyping of human apolipoprotein E by gene amplification and cleavage with Hha I. *J. Lipid Res.* 31:545–548.
6. Ruzicka, V., W. März, A. Russ, and W. Gross. 1992. Apolipoprotein B(Arg3500 to Gln) allele specific polymerase chain reaction: large-scale screening of pooled blood samples. *J. Lipid Res.* 33:1563–1567.
7. Schuster, H., G. Rauh, S. Müller, C. Keller, G. Wolfram, and N. Zöllner. 1992. Allele-specific and asymmetric polymerase chain reaction amplification in combination: a one step polymerase chain reaction protocol for rapid diagnosis of familial defective apolipoprotein B-100. *Anal. Biochem.* 204:22–25.
8. Hansen, P. S., N. Rüdiger, A. Tybjaerg-Hansen, O. Faergeman, and N. Gregersen. 1991. Detection of the apoB-3500 mutation (glutamine for arginine) by gene amplification and cleavage with MspI. *J. Lipid Res.* 32:1229–1233.
9. Miserez, A. R., H. Schuster, N. Chiodetti, and U. Keller. 1993. Polymorphic Haplotypes and recombination rates at the LDL receptor gene locus in subjects with and without familial hypercholesterolemia who are from different populations. *Am. J. Hum. Genet.* 52:808–826.
10. Miserez, A. R. and U. Keller. 1995. Differences in the phenotypic characteristics of subjects with familial defective apolipoprotein B-100 and familial hypercholesterolemia. *Arterioscler. Thromb. Vasc. Biol.* 15:1719–1729.
11. Hua, X., J. Sakai, Y. K. Ho, J. L. Goldstein, and M. S. Brown. 1995. Hairpin orientation of sterol regulatory element-binding protein-2 in cell membranes as determined by protease protection. *J. Biol. Chem.* 270:29422–29427.
12. Hua, X., C. Yokoyama, J. Wu, M. R. Briggs, M. S. Brown, J. L. Goldstein, and X. Wang. 1993. SREBP-2, a second basic-helix-loop-helix-leucine zipper protein that stimulates transcription by binding to a sterol regulatory element. *Proc. Natl. Acad. Sci. USA* 90:11603–11607.
13. Oberhänsli, I., D. Pometta, H. Micheli, L. Raymond, and A. Suenram. 1982. Lipid, lipoprotein and apo-A and apo-B lipoprotein distribution in Italian and Swiss schoolchildren. The Geneva Survey. *Pediatr. Res.* 16:665–669.
14. Burnand, B., V. Wietlisbach, W. Riesen, G. Noseda, M. Barazzoni, M. Rickenbach, and F. Gutzwiller. 1993. Lipides sanguins dans la population suisse: enquête MONICA 1988–89. *Schweiz. Med. Wschr.* 123(Suppl.48): 29–37.
15. Tontonoz, P., J. B. Kim, R. A. Graves, and B. M Spiegelman. 1993. ADD1: a novel helix-loop-helix transcription factor associated with adipocyte determination and differentiation. *Mol. Cell. Biol.* 13:4753–4759.
16. Yokoyama, C., X. Wang, M. R. Briggs, A. Admon, J. Wu, X. Hua, and J. L. Goldstein. 1993. SREBP-1, a basic-helix-loop-helix-leucine zipper protein that controls transcription of the low density lipoprotein receptor gene. *Cell* 75:187–197.
17. Kan, H. Y., P. Pissios, J. Chambaz, and V. I. Zannis. 1999. DNA binding specificity and transactivation properties of SREBP-2 bound to multiple sites on the human apoA-II promoter. *Nucleic Acids Res.* 27(4):1104–1117.
18. Sakai, J., A. Nohturfft, J. L. Goldstein, and M. S. Brown. 1998. Cleavage of Sterol Regulatory Element-binding Proteins (SREBPs) at Site-1 Requires Interaction with SREBP Cleavage-activating Protein. (Evidence from in vivo competition studies). *J. Biol. Chem.* 273(10):5785–5793.
19. Brown, M. S. and J. L. Goldstein. 1997. The SREBP Pathway: Regulation of Cholesterol Metabolism by Proteolysis of a membrane-bound transcription factor. *Cell* 89:331–340.
20. Hua, X., J. Wu, J. L. Goldstein, M. S. Brown, and H. H. Hobbs. 1995. Structure of the human gene encoding sterol regulatory element binding protein-1 (SREBF1) and localization of SREBF1 and SREBF2 to chromosomes 17p11.2 and 22q13. *Genomics* 25:667–673.
21. Miserez, A. R., G. Cao, L. C. Probst, and H. H. Hobbs. 1997. Structure of the human gene encoding sterol regulatory element binding protein 2 (SREBF2). *Genomics* 40:31–40.

The invention claimed is:

1. A purified oligonucleotide from SREBP-1-exon 18c which is 19 to 30 nucleotides in length and which comprises Seq. Id. No. 3.

2. The purified oligonucleotide of claim 1 including a recognition site for Xmn I in the sequence set forth in Seq. Id. No. 3.

3. A DNA and/or RNA chip which comprises a purified oligonucleotide of claim 1.

4. A DNA and/or RNA chip which comprises a purified oligonucleotide of claim 2.

* * * * *

SEQUENCE LISTING

```
<160> NUMBER OF SEQ ID NOS: 20

<210> SEQ ID NO 1
<211> LENGTH: 19
<212> TYPE: DNA
<213> ORGANISM: Homo sapiens
<220> FEATURE:
<221> NAME/KEY: CDS
<222> LOCATION: (2)..(19)

<400> SEQUENCE: 1 g cac cta ggc aaa ggc ttc                                          19
  His Leu Gly Lys Gly Phe
  1               5

<210> SEQ ID NO 2
<211> LENGTH: 6
<212> TYPE: PRT
<213> ORGANISM: Homo sapiens

<400> SEQUENCE: 2

His Leu Gly Lys Gly Phe
1               5

<210> SEQ ID NO 3
<211> LENGTH: 19
<212> TYPE: DNA
```

```
<213> ORGANISM: Homo sapiens
<220> FEATURE:
<221> NAME/KEY: CDS
<222> LOCATION: (2)..(19)

<400> SEQUENCE: 3 g cac cta ggg aaa ggc ttc                                            19
  His Leu Gly Lys Gly Phe
    1               5

<210> SEQ ID NO 4
<211> LENGTH: 6
<212> TYPE: PRT
<213> ORGANISM: Homo sapiens

<400> SEQUENCE: 4

His Leu Gly Lys Gly Phe
  1               5

<210> SEQ ID NO 5
<211> LENGTH: 19
<212> TYPE: DNA
<213> ORGANISM: Homo sapiens

<400> SEQUENCE: 5
ctgctgccgc caacctaca                                                 19

<210> SEQ ID NO 6
<211> LENGTH: 7
<212> TYPE: PRT
<213> ORGANISM: Homo sapiens

<400> SEQUENCE: 6

Ala Ala Ala Ala Asn Leu Gln
  1               5

<210> SEQ ID NO 7
<211> LENGTH: 19
<212> TYPE: DNA
<213> ORGANISM: Homo sapiens

<400> SEQUENCE: 7
ctgctgccgg caacctaca                                                 19

<210> SEQ ID NO 8
<211> LENGTH: 7
<212> TYPE: PRT
<213> ORGANISM: Homo sapiens

<400> SEQUENCE: 8

Ala Ala Ala Gly Asn Leu Gln
  1               5

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 9
ttattaataa tctgggtttt gtgtc                                          25

<210> SEQ ID NO 10
<211> LENGTH: 25
```

```
<212> TYPE: DNA
<213> ORGANISM: Artificial Sequence
<220> FEATURE:
<223> OTHER INFORMATION: Description of Artificial Sequence: PCR Primer

<400> SEQUENCE: 10
gggaagagct aagttaaaag ttgtg                                           25

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: PCR Primer

<400> SEQUENCE: 11
cggaattctg aaattattta taatctgggt tttgtgtc                             38

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: PCR Primer

<400> SEQUENCE: 12
cggaattcat cggggaagag ctaagttaaa agttgtg                              37

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 13
gccagtgacc attaacacct tttga                                           25

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 14
tcgtcttcaa agcctgcctc agtggctggc                                      30

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 15
cggaattcgc cagtgaccat taacaccttt tga                                  33

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 16
```

```
cggaattctg cagcaagcca gtcatcagca gct                                        33
```

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 17

```
cggaattctg gtctcactgt gttttcactc atc                                        33
```

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 18

```
cggaattcgc cagggctgac aagccttttc tca                                        33
```

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: PCR Primer

<400> SEQUENCE: 19

```
gccagaggag attttgcagc tgctgccggc aacctacaaa cctgcc                          46
```

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: PCR Primer

<400> SEQUENCE: 20

```
ggcaggtttg taggttgccg gcagcagctg caaaatctcc tctggc                          46
```